United States Patent
Ellington et al.

(10) Patent No.: US 11,369,811 B2
(45) Date of Patent: Jun. 28, 2022

(54) COMPOSITIONS FOR SHAPING OR ALTERING THE SHAPE OF HAIR

(71) Applicant: L'OREAL, Paris (FR)

(72) Inventors: Angela Ellington, Savannah, GA (US); Eric Osei-Acquah, Lynwood, IL (US); Frederic Cervantes, Westfield, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/536,957

(22) PCT Filed: Dec. 17, 2015

(86) PCT No.: PCT/US2015/066463
§ 371 (c)(1),
(2) Date: Jun. 16, 2017

(87) PCT Pub. No.: WO2016/100714
PCT Pub. Date: Jun. 23, 2016

(65) Prior Publication Data
US 2017/0361129 A1 Dec. 21, 2017

Related U.S. Application Data

(60) Provisional application No. 62/094,712, filed on Dec. 19, 2014.

(51) Int. Cl.
*A61Q 5/04* (2006.01)
*A61K 8/19* (2006.01)
*A61K 8/41* (2006.01)
*A61K 8/81* (2006.01)
*A61Q 5/06* (2006.01)
*A45D 7/06* (2006.01)
*A61K 8/90* (2006.01)

(52) U.S. Cl.
CPC ............... *A61Q 5/04* (2013.01); *A45D 7/06* (2013.01); *A61K 8/19* (2013.01); *A61K 8/416* (2013.01); *A61K 8/817* (2013.01); *A61K 8/90* (2013.01); *A61Q 5/06* (2013.01)

(58) Field of Classification Search
CPC ... A61Q 5/04; A61Q 5/06; A45D 7/06; A61K 8/19; A61K 8/416; A61K 8/817; A61K 8/90
See application file for complete search history.

(56) References Cited

U.S. PATENT DOCUMENTS

| 4,175,572 | A | | 11/1979 | Hsiung et al. |
| 4,663,158 | A | * | 5/1987 | Wolfram |
| 5,293,885 | A | * | 3/1994 | Darkwa |
| 2004/0166074 | A1 | * | 8/2004 | Darkwa |
| 2012/0114584 | A1 | | 5/2012 | Woghiren et al. |

FOREIGN PATENT DOCUMENTS

| EP | 0943315 A2 | 9/1999 |
| EP | 1961450 A1 | 8/2008 |
| WO | 2014/131469 A1 * | 9/2014 |

OTHER PUBLICATIONS

International Search Report and Written Opinion for PCT/US2015/066463, dated Feb. 26, 2016.
Todd, Charles, et al., "Volatile Silicone Fluids for Cosmetic Formulations," Cosmetics and Toiletries, vol. 91, Jan. 1976, pp. 29-32.
International Preliminary Report on Patentability for PCT/US2015/066463, dated Jun. 29, 2017.
Translation of Brazilian Office Action for counterpart Application No. BR112017013128-5, dated Sep. 23, 2020.

* cited by examiner

*Primary Examiner* — Alma Pipic
(74) *Attorney, Agent, or Firm* — The Marbury Law Group, PLLC

(57) ABSTRACT

Disclosed herein is an agent for shaping or altering the shape of hair, such as by straightening or relaxing hair, the agent comprising: A. a hair treatment composition containing an alkaline material selected from a hydroxide-containing compound and a carbonate compound; a cationic polymer selected from a quaternary diammonium polycondensate; an amphoteric polymer selected from a quaternary ammonium compound; an organic solvent, and water; and optionally, B. an activator component; wherein the pH of the composition is equal to or greater than 12 and wherein the weight ratio of (b) to (c) ranges from about 1 up to about 3.

34 Claims, 1 Drawing Sheet

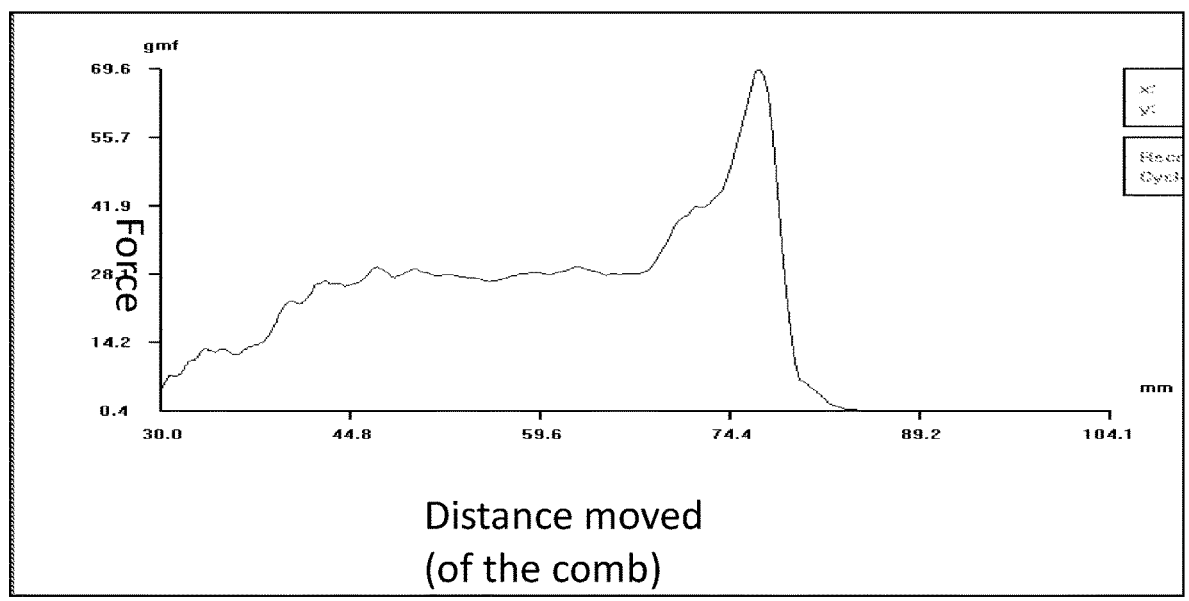

COMPOSITIONS FOR SHAPING OR ALTERING THE SHAPE OF HAIR

FIELD OF THE INVENTION

The present application relates to hair cosmetic compositions for use on keratinous substrates. In particular, it relates to compositions and methods for shaping or altering the shape of hair, such as by relaxing or straightening hair.

BACKGROUND OF THE INVENTION

Cosmetic and personal care products for use on keratinous substrates such as skin and hair are designed to achieve and provide certain benefits and attributes such as efficaciousness, cosmeticity, desirable texture, stable formulations, and ease and convenience of use and application. Thus, in order to meet changing consumer needs and preferences, manufacturers of such products continuously seek to re-formulate and create new products with enhanced efficacy, while still remaining safe to use, as well as improve the manufacture, transport, and storage of these products. In addition, manufacturers continue to test the use of new raw materials and ingredients or new product forms that would help deliver the desired attributes and properties. However, in doing so, formulation challenges are often encountered. For example, re-formulating existing products may adversely impact certain product attributes and properties such as viscosity, texture, stability and efficacy.

One area where manufacturers are always seeking to provide improved consumer and cosmetic products is in the area of styling or altering the configuration/shape of hair such as hair on human heads. There are many techniques and compositions for styling or altering the appearance and shape of hair. In today's market, there is an increasing demand for the hair care products referred to as "hair relaxers" or "hair straighteners" which can relax or straighten curly or kinky hair, including wavy hair. Straightening or relaxing the curls of very curly hair may increase the manageability and ease of styling of such hair. Hair relaxers may either be applied in a hair salon by a professional or in the home by the individual consumer.

One type of composition that can be applied onto hair in order to change its shape and make it more manageable is an alkaline composition. Alkaline hair relaxing/straightening consists of hydrolysis of the keratin of the hair with various alkaline agents, such as inorganic hydroxides, for instance sodium hydroxide, or organic hydroxides, such as guanidine hydroxide, or organic amines. Hair relaxing/straightening products that employ sodium hydroxide or potassium hydroxide are also called lye-based products and products that use other alkaline agents such as lithium hydroxide, organic hydroxides and other non-hydroxide compounds, for example, organic amines, generally fall under the category of no-lye products. Lye-based products are generally employed as one-component systems ("no mix" systems).

One other type of product based on a no-lye composition employs guanidine hydroxide as the active agent for straightening or relaxing hair. Guanidine hydroxide is unstable and therefore, most commercial products of this type are based on a two-component system ("mix" system) containing a composition comprising a hydroxide-based compound such as calcium hydroxide and a second composition comprising a carbonate compound such as guanidine carbonate. The two compositions are mixed prior to relaxing or straightening the hair in order to produce guanidine hydroxide in the resulting mixture or ready to use composition.

Generally, alkaline hair relaxing/straightening products can be made available in liquid, lotion or cream form in order to facilitate their application onto hair. Thus, hair relaxing and straightening products should have a viscosity such that they do not run or drip when applied onto the hair fibers so as to avoid contacting the skin with the product and to ensure the deposition of the alkaline agents onto the hair fibers. The process of treating hair with the above-described relaxing/straightening products may also include heating and/or physically changing the shape of the hair by use of a brush or a comb.

Still, it is desirable to find alternatives and/or improvements to the alkaline lye- and no-lye-based products and process described above which may damage to the hair by weakening and/or causing dryness of the hair fibers. However, the discovery of new compositions and processes for changing the shape of hair may pose challenges to manufacturers and formulators because the incorporation of new ingredients into the compositions may negatively impact their performance, cosmetic attributes, and formulation stability. New processes of treating and changing the shape of hair may also impact the performance of the compositions, processing times and quality of use.

Attributes of products for treating hair that can affect their performance and/or desirability to consumers include texture, form or appearance (liquid, cream, gel, lotion or powder), ease of application, viscosity or rheology, ease of use, storage, effect on the quality and feel of the hair, and safety. For example, hair relaxing and straightening products should have a viscosity such that they do not have a thin consistency. This means that they should not run or drip readily when applied onto the hair fibers so as to avoid contacting the skin with the product and to ensure that the active or straightening agents in the product are deposited onto the hair fibers and remain on the fibers during the straightening/relaxation period.

The present invention provides a hair treatment agent comprising a composition ("composition (A)") containing an alkaline material selected from at least one hydroxide-containing compound and at least one carbonate compound, a cationic polymer selected from at least one quaternary diammonium polycondensate, an amphoteric polymer selected from at least one quaternary ammonium compound, an organic solvent, and water; wherein the pH of the composition is equal to or greater than 12 and wherein the weight ratio of (b) to (c) ranges from about 1 up to about 3. The hair treatment agent can further comprise an activator component. Depending on the selection of the alkaline material, the activator component can contain a hydroxide-containing compound or a carbonate compound. The agent can also optionally contain a non-alkoxylated fatty substance that is liquid at room temperature, and/or an alkoxylated nonionic surfactant, and/or a fatty alcohol that is solid at room temperature. It has now been surprisingly and unexpectedly discovered that said agent can be used to shape or alter the shape of hair such as by relaxing or straightening hair.

It was also surprisingly and unexpectedly discovered that the composition (A) of the present invention is stable, i.e., there is no phase separation, even when cationic and amphoteric polymers are employed in a high-pH composition. In addition, composition (A) and/or hair treatment agent have a viscosity their corresponds to a non-drip, and homogeneous consistency that facilitates the ease of application onto hair fibers, thereby resulting in an effective process of shaping or altering the shape of hair.

BRIEF SUMMARY OF THE INVENTION

The present invention relates to an agent for shaping or altering the shape of hair, the agent comprising:
A. a hair treatment composition containing:
 (a) at least one alkaline material selected from:
  (i) at least one hydroxide-containing compound selected from alkali metal hydroxides, alkaline-earth metal hydroxides, transition metal hydroxides, and mixtures thereof; and
  (ii) at least one carbonate compound selected from lithium carbonate, sodium carbonate, potassium carbonate, guanidine carbonate, and mixtures thereof;
 (b) at least one cationic polymer selected from at least one quaternary diammonium polycondensate composed of repeat units corresponding to the formula (a) below:

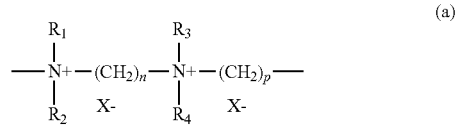

(a)

in which R1, R2, R3 and R4, which are identical or different, denote an alkyl or hydroxyalkyl group having from 1 to 4 carbon atoms, n and p are integers that vary from 2 to 6 and X— is a mineral or organic acid anion;
 (c) at least one amphoteric polymer selected from at least one quaternary ammonium compound;
 (d) at least one organic solvent; and
 (e) water;
 wherein the weight ratio of (b) to (c) ranges from about 1 up to about 3; and optionally,
B. an activator component;
 wherein the pH of the agent is equal to or greater than 12.

The invention also relates to a process for shaping hair or altering the shape of hair, involving applying the above-described composition/agent onto hair.

The hair treatment compositions of the present invention are stable over time and do not undergo phase separation.

It is to be understood that both the foregoing general description and the following detailed description are exemplary and explanatory only, and are not restrictive of the invention.

BRIEF DESCRIPTION OF THE DRAWING

FIG. 1 represents a sample chart or combing profile for wet combing work and peak combing force measurements obtained when a combed device is passed through wet hair.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

The term "comprising" (and its grammatical variations) as used herein is used in the inclusive sense of "having" or "including" and not in the exclusive sense of "consisting only of".

"Keratin fiber" as used herein, includes, but is not limited to hair, such as hair on the human head and eyelashes.

As used herein, the terms "applying a composition onto keratin fibers" and "applying a composition onto hair" and variations of these phrases are intended to mean contacting the fibers or hair, with at least one of the compositions of the invention, in any manner.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

The term "stable" as used herein means that the composition does not exhibit phase separation and/or crystallization.

The term "treat" (and its grammatical variations) as used herein refers to the application of the compositions of the present invention onto keratin fibers such as hair.

"Wax" as used herein means a hydrocarbon material, natural or synthetic, and having a melting point in the ranges disclosed below. Polymers and copolymers are included in this definition. Wax as used herein may also include a material composed of several components, including wax esters such as those derived from carboxylic acids and fatty alcohols, wax alcohols, and hydrocarbons.

"Volatile", as used herein, means having a flash point of less than about 100° C.

"Non-volatile", as used herein, means having a flash point of greater than about 100° C.

"Substituted" as used herein, means comprising at least one substituent. Non-limiting examples of substituents include atoms, such as oxygen atoms and nitrogen atoms, as well as functional groups, such as acyloxyalkyl groups, carboxylic acid groups, amine or amino groups, acylamino groups, amide groups, halogen containing groups, ester groups, thiol groups, sulphonate groups, thiosulphate groups, siloxane groups, and polysiloxane groups. The substituent(s) may be further substituted.

The terms "organic compound" and "having an organic structure" mean compounds containing carbon atoms and hydrogen atoms and optionally heteroatoms such as S, O, N or P, alone or in combination.

The compositions and methods of the present invention can comprise, consist of, or consist essentially of the essential elements and limitations of the invention described herein, as well as any additional or optional ingredients, components, or limitations described herein or otherwise useful.

In an embodiment of the present invention, the agent for shaping or altering the shape of hair comprises:
A. a hair treatment composition containing:
 (a) from about 2% to about 5% by weight of at least one alkaline material selected from:
  (i) at least one hydroxide-containing compound selected from alkali metal hydroxides, alkaline-earth metal hydroxides, transition metal hydroxides, and mixtures thereof; and
  (ii) at least one carbonate compound selected from lithium carbonate, sodium carbonate, potassium carbonate, guanidine carbonate, and mixtures thereof;
 (b) from about 0.1% to about 5% by weight of at least one cationic polymer selected from at least one quaternary diammonium polycondensate composed of repeat units corresponding to the formula (a) below:

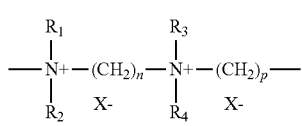

(a)

in which R1, R2, R3 and R4, which are identical or different, denote an alkyl or hydroxyalkyl group having from 1 to 4 carbon atoms, n and p are integers that vary from 2 to 6 and X— is a mineral or organic acid anion;
(c) from about 0.1% to about 5% by weight of at least one amphoteric polymer selected from at least one quaternary ammonium compound;
(d) at least one organic solvent;
(e) water;
(f) optionally, at least one non-alkoxylated fatty substance that is liquid at room temperature and present in an amount of from about 7% to about 30% by weight;
(g) optionally, at least one alkoxylated nonionic surfactant and present in an amount of from about 0.75% to about 10% by weight; and
(h) optionally, at least one fatty alcohol that is solid at room temperature and present in an amount of from about 0.75% to about 10% by weight;
all weights above being based on the total weight of the composition;
wherein the pH of the composition is from about 13 to about 14;
wherein the weight ratio of (b) to (c) ranges from about 1 to about 2.5.

In any one of the above-described compositions of the invention, the at least one organic solvent includes organic solvents such as C2 to C4 mono-alcohols, such as ethanol, isopropyl alcohol, butanol, polyols such as C2-C6 glycols e.g., propylene glycol, butylene glycol, pentylene glycol, hexylene glycol, glycerol, volatile polyol ethers, volatile glycol ethers, acetone, propylene carbonate, benzyl alcohol, and mixtures thereof.

The compositions of the invention have a thick, smooth, creamy and homogenous texture, i.e., not lumpy and/or thin, are easy to apply and spread on the hair, and did not easily drip or run off of the hair fibers. The non-drip consistency of the compositions of the present invention is desirable because it helps prevent the compositions from coming in contact with and causing irritation on the skin or scalp.

It was surprisingly and unexpectedly discovered that the composition of the invention was stable over time, did not exhibit phase separation, and retained the straightening or relaxing activity of the alkaline material such that hair was effectively or satisfactorily straightened or relaxed. In addition, the association of the cationic polymer and the amphoteric polymer of the compositions of the invention resulted in less scalp irritation, despite the highly alkaline nature of the compositions.

Furthermore, it was surprisingly and unexpectedly discovered that even when a liquid fatty substance such as an oil was present even at high levels in the compositions of the present invention, the compositions still have a creamy texture are easy to apply and spread on the hair, and are not sticky or tacky or greasy.

Alkaline Material

The present invention employs at least one alkaline material selected from at least one hydroxide-containing compound and at least one carbonate compound.

The at least one hydroxide-containing compound may be selected from alkali metal hydroxides, alkaline-earth metal hydroxides, transition metal hydroxides, and mixtures thereof.

In some embodiments, the at least one hydroxide-containing compound is selected from sodium hydroxide, potassium hydroxide, lithium hydroxide, calcium hydroxide, magnesium hydroxide, barium hydroxide, strontium hydroxide, manganese hydroxide, zinc hydroxide, and mixtures thereof.

In other embodiments, the at least one hydroxide-containing compound is selected from sodium hydroxide, potassium hydroxide, lithium hydroxide, calcium hydroxide, and mixtures thereof.

According to certain embodiments, the at least one hydroxide-containing compound is selected from sodium hydroxide, potassium hydroxide, and mixtures thereof.

According to other embodiments, the at least one hydroxide-containing compound is lithium hydroxide.

In yet other embodiments, the at least one hydroxide-containing compound is calcium hydroxide.

In some embodiments, the at least one hydroxide-containing compound is guanidine hydroxide.

In particular embodiments, guanidine hydroxide is formed from the combination of a carbonate compound such as guanidine carbonate, and a hydroxide compound such as calcium hydroxide.

The amount of the at least one hydroxide-containing compound is preferably such that the composition of the present invention has a pH of equal to or greater 12.

The at least one carbonate compound of the present invention may be selected from lithium carbonate, sodium carbonate, potassium carbonate, guanidine carbonate, and mixtures thereof.

One particularly preferred carbonate compound for use in the present invention is guanidine carbonate.

The amount of the at least one carbonate compound is preferably such that the composition of the present invention has a pH of equal to or greater 12.

The at least one alkaline material can be employed in the compositions of the present invention in an amount ranging from about 0.1 to about 30% by weight, based on the total weight of the composition, including all ranges and subranges therebetween.

When the at least one alkaline material is selected from at least one hydroxide-containing compound, the at least one hydroxide-containing compound can be employed in the compositions of the present invention in an amount ranging from about 0.1 to about 30% by weight of active material, based on the total weight of the composition, including all ranges and subranges therebetween.

In certain embodiments, the at least one hydroxide-containing compound is employed in the compositions of the present invention in an amount ranging from about 1 to about 20% by weight, preferably from about 1.5 to about 10% by weight, or more preferably from about 2 to about 5% by weight, or even more preferably from about 2 to about 3% by weight of active material and based on the total weight of the composition, including all ranges and subranges therebetween.

In preferred embodiments, the at least one hydroxide-containing compound is employed in the compositions of the present invention in an amount of about 10%, about 8%, about 7%, about 6.5%, about 6%, about 5.5%, about 5%, about 4.5%, about 4%, about 3.5%, about 3%, about 2.9%, about 2.8%, about 2.7%, about 2.6%, about 2.5%, about 2.4%, about 2.3%, about 2.2%, about 2.1%, about 2%, by weight of active material and based on the total weight of the composition.

When the at least one alkaline material is selected from at least one carbonate compound, the at least one carbonate compound can be employed in the compositions of the present invention in an amount ranging from about 8 to about 30% by weight, preferably from about 8 to about 20% by weight, more preferably from about 10 to about 20% by weight, based on the total weight of the composition, including all ranges and subranges therebetween.

In preferred embodiments, the at least one carbonate compound is employed in an amount of about 8%, or about 10%, or about 15%, by weight, based on the total weight of the composition.

Cationic Polymer

The cationic polymer of the present invention is selected from at least one quaternary diammonium polycondensate composed of repeat units corresponding to the formula (a) below:

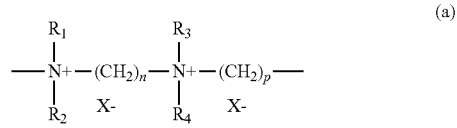

(a)

in which R1, R2, R3 and R4, which are identical or different, denote an alkyl or hydroxyalkyl group having from 1 to 4 carbon atoms, n and p are integers that vary from 2 to 6 and X— is a mineral or organic acid anion.

In at least one embodiment, the compound of formula (a) is that for which R1, R2, R3 and R4 represent a methyl group and n=3, p=6 and X—Cl, that is to say the hexadimethrine chloride known as "Hexadimethrine chloride" according to the INCI (CTFA) nomenclature and known under the tradename MEXOMERE PO.

According to at least one embodiment, the polycondensate that may be used in the present disclosure has a cationic charge greater than 5 meq/g, such as greater than 6 meq/g. This charge density may be determined either by calculation from the structure of the polymer or experimentally via the Kjeldahl method.

The cationic polymer of the present invention selected from at least one quaternary diammonium polycondensate composed of repeat units corresponding to the formula (a) above is employed in the hair treatment compositions of the present invention in an amount ranging from about 0.1 to about 12% by weight, preferably from about 0.1 to about 5% by weight, or more preferably from about 0.1 to about 2.5% by weight, or even more preferably from about 0.1 to about 2% by weight, such as from about 0.2 to about 1% by weight, with all weights of the cationic polymer being the weight of the active material and based on the total weight of the composition, including all ranges and subranges therebetween.

In certain embodiments, the cationic polymer of the present invention selected from at least one quaternary diammonium polycondensate composed of repeat units corresponding to the formula (a) above is employed in an amount of about 12%, 10%, 8%, 6%, 4%, 3%, 2%, 1%, 0.95%, 0.9%, 0.85%, 0.8%, 0.75%, 0.7%, 0.65%, 0.6%, 0.55% 0.5%, 0.45%, 0.4%, 0.35%, 0.3%, 0.25%, 0.2%, 0.15%, 0.1%, by weight, with all weights of the cationic polymer being the weight of the active material and based on the total weight of the composition.

Amphoteric Polymer

The at least one amphoteric polymer of the present invention is selected from quaternary ammonium compounds. The amphoteric polymers of the present invention may include ampholytic polymers that are employed as conditioning agents in cosmetic and hair compositions.

Suitable examples of the amphoteric polymer selected from quaternary ammonium compounds are include copolymeric and polymeric compounds comprised of:

(A) about 1 to about 99 mol percent of at least one monomer selected from the group consisting of alkyl acrylamidopropyl-dimethyl ammonium halides, alkyl methacrylamidopropyidimethyl ammonium halides, alkyl acryloyloxyethyl dimethyl ammonium halides, alkyl methacryloyloxyethyl dimethyl ammonium halides, methacrylamidopropylammonium halides, and dialkyl diallyl ammonium halides;

(B) about 1 to about 99 mol percent of an ethylenically unsaturated acid containing monomer selected from the group consisting of carboxylic acids and sulfonic acids, preferably at least one monomer selected from the group consisting of acrylic acid (AA), methacrylic acid (MAA), 2-acrylamido-2-methylpropane sulfonic acid (AMPSA) 2-methacrylamido-2-methylpropane sulfonic acid (MAMPSA), n-methacrylam idopropyl,n,n-dimethyl, amino acetic acid, n-acrylam idopropyl,n,n-dimethyl, amino acetic acid, n-methacryloyloxyethyl,n,n-dimethyl, amino acetic acid, and n-acryloyloxyethyl,n,n-dimethyl, amino acetic acid; and (C) about 0 to about 80 mol percent of at least one monomer selected from the group consisting of C1-C22 straight or branched chain alkyl acrylate or methacrylate, a C1-C22 straight or branched chain n-alkyl acrylamide or methacrylamide, acrylamide methylacrylamide, n-vinylpyrrolidone, vinyl acetate or ethoxylated and propoxylated acrylate or methacrylate; with a weight average molecular weight of, as determined by viscometry, of at least about 50,000.

of at least one monomer are dialkyldiallyl ammonium halide copolymers and methacrylamidopropylammonium halide copolymers.

In certain embodiments of the present invention, the amphoteric polymer selected from quaternary ammonium compounds is chosen from dialkyldiallyl ammonium halide copolymers such as copolymers of dimethyldiallyl ammonium chloride (DMDAAC).

In other embodiments of the present invention, the amphoteric polymer selected from quaternary ammonium compounds is chosen from polymeric methacrylamidopropylammonium halides.

In certain embodiments, the amphoteric polymer selected from quaternary ammonium compounds is chosen from:
the copolymer of diallyldimethylammonium chloride and acrylic acid, such as the one known under the INCI name of polyquaternium-22 and tradename of MERQUAT 280 NP POLYMER;
the terapolymer of diallyldimethylammonium chloride, acrylic acid, and acrylamide such as the one known under the INCI name of polyquaternium-39 and tradename of MERQUAT 3330 DRY POLYMER or MERQUAT 3330pr POLYMER;
the terpolymer of acrylic acid, methyl acrylate and methacrylamidopropyltrimethyl ammonium chloride (MAPTAC), such as the one known under the INCI name of polyquaternium-47 and the tradename MERQUAT 2001 POLYMER or MERQUAT 2001N POLYMER;

the terpolymer of methacrylamidopropyltrimethyl ammonium chloride (MAPTAC), acrylamide, and acrylic acid such as the one known under the INCI name of polyquaternium-53 and the tradename MERQUAT 2003PR POLYMER;

all commercially sold by the company Nalco (Lubrizol).

In preferred embodiments, the amphoteric polymer selected from quaternary ammonium compounds is the copolymer of diallyldimethylammonium chloride and acrylic acid, such as the one known under the INCI name of polyquaternium-22 and tradename of MERQUAT 280 NP POLYMER and commercially sold by the company Nalco (Lubrizol).

The amphoteric polymer selected from quaternary ammonium compounds is employed in the hair treatment compositions of the present invention in an amount ranging from about 0.1 to about 12% by weight, preferably from about 0.1 to about 5% by weight, or more preferably from about 0.1 to about 2.5% by weight, or even more preferably from about 0.1 to about 2% by weight, such as from about 0.2 to about 1% by weight, with all weights of the amphoteric polymer being the weight of the active material and based on the total weight of the composition, including all ranges and subranges therebetween. In certain embodiments, the amphoteric polymer selected from quaternary ammonium compounds is employed in the compositions of the present invention is employed in an amount of about 12%, 10%, 8%, 6%, 4%, 3%, 2%, 1%, 0.95%, 0.9%, 0.85%, 0.8%, 0.75%, 0.7%, 0.65%, 0.6%, 0.55% 0.5%, 0.45%, 0.4%, 0.35%, 0.3%, 0.25%, 0.2%, 0.15%, 0.1%, by weight, with all weights of the amphoteric polymer being the weight of the active material and based on the total weight of the composition.

In preferred embodiments, the amphoteric polymer selected from quaternary ammonium compounds is the copolymer of diallyldimethylammonium chloride and acrylic acid, such as the one known under the INCI name of polyquaternium-22 and tradename of MERQUAT 280 NP POLYMER and commercially sold by the company Nalco (Lubrizol).

The amphoteric polymer selected from quaternary ammonium compounds is employed in the hair treatment compositions of the present invention in an amount ranging from about 0.1 to about 12% by weight, preferably from about 0.1 to about 5% by weight, or more preferably from about 0.1 to about 2.5% by weight, or even more preferably from about 0.1 to about 2% by weight, such as from about 0.2 to about 1% by weight, with all weights of the amphoteric polymer being the weight of the active material and based on the total weight of the composition, including all ranges and subranges therebetween. In certain embodiments, the amphoteric polymer selected from quaternary ammonium compounds is employed in the compositions of the present invention in an amount of about 12%, 10%, 8%, 6%, 4%, 3%, 2%, 1%, 0.95%, 0.9%, 0.85%, 0.8%, 0.75%, 0.7%, 0.65%, 0.6%, 0.55% 0.5%, 0.45%, 0.4%, 0.35%, 0.3%, 0.25%, 0.2%, 0.15%, 0.1%, by weight, with all weights of the amphoteric polymer being the weight of the active material and based on the total weight of the composition.

Organic Solvents

The hair treatment compositions of the present invention comprise at least one organic solvent.

Suitable organic solvents may be chosen from volatile and nonvolatile organic solvents.

Suitable organic solvents for use in the present invention are C1-C4 lower alcohols, glycols, polyols, and polyol ethers. Examples of organic solvents include, but are not limited to, ethanol, isopropyl alcohol, benzyl alcohol, phenyl ethyl alcohol, propylene glycol, pentylene glycol, hexylene glycol, glycerol, and mixtures thereof.

Other suitable organic solvents include glycol ethers, for example, ethylene glycol and its ethers such as ethylene glycol monomethyl ether, ethylene glycol monopropyl ether, ethylene glycol monobutyl ether, propylene glycol and its ethers, such as propylene glycol monomethyl ether, propylene glycol monopropyl ether, propylene glycol monobutyl ether, dipropylene glycol and diethylene glycol alkyl ethers, such as diethylene glycol monoethyl ether, diethylene glycolmonobutyl ether, and dipropylene glycol n-butyl ether. Glycol ethers are commercially available from The Dow Chemical Company under the DOW E-series and DOW P-series. One preferred glycol ether for use in the present invention is dipropylene glycol n-butyl ether, known under the tradename of DOWANOL DPnB.

The amount of the organic solvent/compound present in the compositions of the present invention can range from about 0.5% to about 60%, or from about 0.5% to about 40%, or from about 0.5% to about 30%, or from about 0.5% to about 20%, and in some embodiments, from about 0.5% to about 15%, by weight, or preferably from about 1% to about 10%, by weight, or more preferably from about 1.5% to about 8%, by weight, or from about 1.5% to about 6%, by weight, including all ranges and subranges there-between, based on the total weight of the composition.

In some embodiments, the amount of the organic solvent/compound present in the compositions of the present invention is at about 1.5%, about 2%, about 2.5%, about 3%, about 3.5%, about 4%, about 4.5%, about 5%, about 5.5% or about 6% by weight, including all ranges and subranges there-between, based on the total weight of the composition.

In certain embodiments, compositions of the present invention comprise both water and organic solvents/compounds selected from volatile organic solvents, non-volatile organic solvents, and mixtures thereof.

Preferred examples of organic solvents/compounds include organic solvents such as C2 to C4 mono-alcohols, such as ethanol, isopropyl alcohol, butanol, polyols such as C2-C6 glycols e.g., propylene glycol, butylene glycol, pentylene glycol, hexylene glycol, glycerol, volatile polyol ethers, volatile glycol ethers, acetone, propylene carbonate, benzyl alcohol, and mixtures thereof. In certain embodiments, when the organic solvent is a volatile organic solvent, it is preferred that the amount of volatile organic solvent/compound does not exceed 55% by weight, relative to the weight of the composition of the present invention.

In other certain embodiments, it is preferred that the amount of volatile organic solvent/compound does not exceed 20% by weight, relative to the weight of the composition of the present invention.

In yet other certain embodiments, it is preferred that the amount of volatile organic solvent/compound does not exceed 10% by weight, relative to the weight of the composition of the present invention.

In preferred embodiments, the amount of volatile organic solvent/compound does not exceed 6% by weight, relative to the weight of the composition of the present invention.

In preferred embodiments of the present invention, the at least one organic solvent is chosen from ethanol, glycol ether, for example, dipropylene glycol n-butyl ether, known under the tradename of DOWANOL DPnB, propylene glycol, butylene glycol, pentylene glycol, hexylene glycol, glycerol, and mixtures thereof.

In certain embodiments of the present invention, the at least one organic solvent is chosen from ethanol.

Water

The hair treatment compositions of the present invention contain water. Water can be present in the amount of about 95%, 90%, 80%, 70%, 60%, 50%, 40%, 30%, 20%, 10%, 5% by weight or less, based on the total weight of the compositions. Additionally, water can be present in the compositions of the present invention in the amount of from about 20% to about 95% by weight, or from about 40% to about 90% by weight, or from about 50% to about 80% by weight, based on the total weight of the compositions, including all ranges and subranges therebetween In other embodiments, water can be present in the compositions of the present invention in the amount of at least about 95%, 90%, 80%, 70%, 60%, 50%, 45%, 40%, 30%, 20%, 10%, 5% by weight or less, based on the total weight of the compositions.

Activator Component

The agents for shaping or altering the shape of hair and the hair treatment compositions of the present invention may further comprise an activator component.

The activator component may comprise either at least one non-hydroxide-containing compound or at least one carbonate compound, and optionally, a solvent.

Examples of the at least one non-hydroxide-containing compounds and of the at least one carbonate compounds that may be present in the activator component include those non-hydroxide-containing and carbonate compounds that may be employed in the hair treatment compositions of the present invention as described above.

In certain embodiments, the at least one hydroxide-containing compound is employed in the compositions of the present invention in an amount ranging from about 0.1 to about 30% by weight, or from about 1 to about 20% by weight, preferably from about 1.5 to about 10% by weight, or more preferably from about 2 to about 5% by weight, or even more preferably from about 2 to about 3% by weight of active material and based on the total weight of the activator component, including all ranges and subranges therebetween.

In preferred embodiments, the at least one hydroxide-containing compound is employed in an amount of about 10%, about 8%, about 7%, about 6.5%, about 6%, about 5.5%, about 5%, about 4.5%, about 4%, about 3.5%, about 3%, about 2.9%, about 2.8%, about 2.7%, about 2.6%, about 2.5%, about 2.4%, about 2.3%, about 2.2%, about 2.1%, about 2%, by weight of active material and based on the total weight of the activator component.

In other embodiments, the at least one carbonate compound can be employed in the compositions of the present invention in an amount ranging from about 8 to about 30% by weight, preferably from about 8 to about 20% by weight, more preferably from about 10 to about 20% by weight, based on the total weight of the activator component, including all ranges and subranges therebetween.

In preferred embodiments, the at least one carbonate compound is employed in an amount of about 8%, or about 10%, or about 15%, by weight, based on the total weight of the activator component.

The optionally present solvent may be chosen from water, an organic solvent, and mixtures thereof. Examples of organic solvents include those solvents as described above and which may be employed in the hair treatment compositions of the invention.

The activator component may be in liquid, emulsion or powder form.

Non-Alkoxylated Fatty Substance

The hair treatment compositions and agents for shaping or altering the shape of hair of the present invention may also comprise at least one non-alkoxylated fatty substance that is liquid at room temperature (e.g., 25° C.) and at atmospheric pressure, i.e. which has a solubility in water of less than 5 percent by weight, preferably less than 1 percent by weight and even more preferentially less than 0.1 percent by weight. The fatty substances contain in their structure at least one sequence of at least two siloxane groups or a hydrocarbon-based chain comprising at least 6 carbon atoms. In addition, the fatty substances are generally soluble in organic solvents under the same temperature and pressure conditions, for instance chloroform, ethanol, benzene, liquid petroleum jelly (liquid petrolatum) or liquid paraffin or decamethylcyclopentasiloxane.

The term "liquid fatty substance" means a fatty substance that is liquid or pasty at ordinary temperature (25 degrees C.) and at atmospheric pressure (760 mmHg; i.e. $1.013 \times 10^5$ Pa).

The liquid fatty substance(s) are chosen from C6-C16 hydrocarbons, hydrocarbons containing more than 16 carbon atoms, non-silicone oils of plant, mineral or synthetic origin, plant oils of triglyceride type, synthetic triglycerides, fluoro oils, liquid fatty alcohols, liquid fatty acids and liquid esters of a fatty acid and/or of a fatty alcohol other than triglycerides, silicones, and mixtures thereof.

More particularly, the liquid fatty substance(s) are chosen from:

linear or branched, optionally cyclic, C6-C16 lower hydrocarbons, preferably alkanes. Examples that may be mentioned include hexane, undecane, dodecane, tridecane, and isoparaffins, for instance isohexadecane, isododecane and isodecane, linear or branched hydrocarbons of mineral, animal or synthetic origin, containing more than 16 carbon atoms, such as liquid paraffins, liquid petroleum jelly or liquid petrolatum, polydecenes and hydrogenated polyisobutenes such as PARLEAM and squalane.

In one preferred variant, the liquid fatty substance(s) are chosen from liquid paraffin, liquid petroleum jelly, and mixtures thereof.

In another preferred variant, the liquid fatty substance is chosen from mineral oil.

Preferably, the silicones are chosen from liquid polydialkylsiloxanes, especially liquid polydimethylsiloxanes (PDMS) and liquid polyorganosiloxanes comprising at least one aryl group.

These silicones may also be organomodified. The organomodified silicones that may be used in accordance with the invention are liquid silicones as defined previously, comprising in their structure one or more organofunctional groups attached via a hydrocarbon-based group.

Organopolysiloxanes are defined in greater detail in Walter Noll's Chemistry and Technology of Silicones (1968), Academic Press. They can be volatile or nonvolatile. When they are volatile, the silicones are more particularly chosen from those having a boiling point of between 60 degrees centigrade and 260 degrees centigrade, and more particularly still from:

(i) cyclic polydialkylsiloxanes containing from 3 to 7 and preferably from 4 to 5 silicon atoms. These are, for example, octamethylcyclotetrasiloxane sold in particular under the name SILICONE VOLATILE 7207 by Union Carbide or SILBIONE 70045 V2 by Rhodia, decamethylcyclopentasiloxane sold under the name SILICONE VOLATILE 7158 by Union Carbide or SILBIONE 70045 V5 by Rhodia, and dodecamethylcyclopentasiloxane sold under the name SILSOFT 1217 by Momentive Performance Materials, and mixtures thereof.

Mention may also be made of cyclocopolymers of the dimethylsiloxane/methylalkylsiloxane type, such as SILICONE VOLATILE FZ 3109, sold by Union Carbide, of formula:

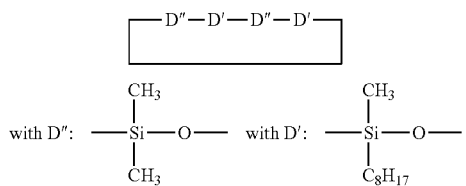

Mention may also be made of mixtures of cyclic polydialkylsiloxanes with organic compounds derived from silicon, such as the mixture of octamethylcyclotetrasiloxane and tetra(trimethylsilyl)pentaerythritol (50/50) and the mixture of octamethylcyclotetrasiloxane and oxy-I,I'-bis(2,2,2', 2',3,3'-hexatrimethylsilyloxy)neopentane;

(ii) volatile linear polydialkylsiloxanes having from 2 to 9 silicon atoms and exhibiting a viscosity of less than or equal to 5×10"6 mVs at 25 degrees centigrade An example is decamethyltetrasiloxane, sold in particular under the name SH 200 by Toray Silicone. Silicones coming within this category are also described in the paper published in Cosmetics and Toiletries, Vol. 91, January 1976, pp. 27-32, Todd and Byers, Volatile Silicone Fluids for Cosmetics. The viscosity of the silicones is measured at 25 degrees centigrade according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:
the SILBIONE oils of the 47 and 70 047 series or the MIRASIL oils sold by Rhodia, such as, for example, the oil 70 047 V 500 000;
the oils of the MIRASIL series sold by Rhodia;
the oils of the 200 series from Dow Corning, such as DC200 having a viscosity of 60 000 mm2/s;
the VICASIL oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

Among the silicones containing aryl groups are polydiarylsiloxanes, in particular polydiphenylsiloxanes and polyalkylarylsiloxanes. Examples that may be mentioned include the products sold under the following names:
the SILBIONE oils of the 70 641 series from Rhodia;
the oils of the RHODORSIL 70 633 and 763 series from Rhodia;
the oil Dow Corning 556 Cosmetic Grade Fluid from Dow Corning;
the silicones of the PK series from Bayer, such as the product PK20;
certain oils of the SF series from General Electric, such as SF 1023, SF 1 154, SF 1250 and SF 1265.

The liquid fatty esters are preferably liquid esters of saturated or unsaturated, linear or branched C1-C26 aliphatic monoacids or polyacids and of saturated or unsaturated, linear or branched C1-C26 aliphatic monoalcohols or polyalcohols, the total number of carbon atoms of the esters being greater than or equal to 10.

Preferably, for the esters of monoalcohols, at least one of the alcohol or of the acid from which the esters of the invention result is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of C4-C22 dicarboxylic or tricarboxylic acids and of C1-C22 alcohols and esters of monocarboxylic, dicarboxylic or tricarboxylic acids and of non-sugar C4-C26 dihydroxy, trihydroxy, tetrahydroxy or pentahydroxy alcohols may also be used.

Mention may be made especially of: diethyl sebacate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

The composition may also comprise, as liquid fatty ester, sugar esters and diesters of C6-C30 and preferably C12-C22 fatty acids. It is recalled that the term "sugar" means oxygen-bearing hydrocarbon-based compounds containing several alcohol functions, with or without aldehyde or ketone functions, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose, lactose and their derivatives, in particular alkyl derivatives, such as methyl derivatives, for example methylglucose.

The esters of sugars and of fatty acids can be chosen in particular from the group consisting of the esters or mixtures of esters of sugars described above and of saturated or unsaturated and linear or branched C6-C30 and preferably C12-C22 fatty acids. If they are unsaturated, these compounds may comprise one to three conjugated or unconjugated carbon-carbon double bonds.

The esters according to this alternative form can also be chosen from mono-, di-, tri- and tetraesters, polyesters and their mixtures.

These esters can, for example, be oleates, laurates, palmitates, myristates, behenates, cocoates, stearates, linoleates, linolenates, caprates, arachidonates or their mixtures, such as, in particular, oleate/palmitate, oleate/stearate or palmitate/stearate mixed esters. More particularly, use is made of mono- and diesters and in particular mono- or di-oleate, -stearate, -behenate, -oleate/palmitate, -linoleate, -linolenate or -oleate/stearate of sucrose, glucose or methylglucose.

Mention may be made, by way of example, of the product sold under the name GLUCATE DO by Amerchol, which is a methylglucose dioleate.

Finally, natural or synthetic esters of monoacids, diacids or triacids with glycerol may also be used.

Among these, mention may be made of plant oils.

As oils of plant origin or synthetic triglycerides that may be used in the composition of the invention as liquid fatty substances, examples that may be mentioned include:

triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, camellia oil, olive oil, caprylic/capric acid triglycerides, for instance those sold by the company Stearineries Dubois or those sold under the names MIGLYOL 810, 812 and 818 by the company Dynamit Nobel, jojoba oil and shea butter oil.

Liquid fatty esters derived from monoalcohols or triglycerides of plant origin will preferably be used as esters according to the invention.

The liquid non-oxyethylenated fatty alcohols that may be used as fatty substances according to the invention advantageously comprise from 8 to 30 carbon atoms.

They may be chosen in particular from unsaturated fatty alcohols and branched saturated fatty alcohols.

These unsaturated liquid fatty alcohols exhibit, in their structures, at least one double or triple bond. Preferably, the fatty alcohols of the invention bear in their structure one or more double bonds. When several double bonds are present, there are preferably 2 or 3 of them and they may or may not be conjugated.

These fatty alcohols may be linear or branched.

They may optionally comprise in their structure at least one aromatic or non-aromatic ring. They are preferably acyclic. More particularly, the liquid unsaturated fatty alcohols of the invention are selected from oleic (or oleyl) alcohol, linoleic (or linoleyl) alcohol, linolenic (or linolenyl) alcohol and undecylenyl alcohol.

Oleyl alcohol is most particularly preferred.

The liquid fatty alcohols may also be branched saturated fatty alcohols.

More particularly, the liquid branched saturated fatty alcohols of the invention are chosen from isostearyl alcohol and octyldodecanol.

According to one preferred embodiment, the liquid fatty substance(s) are chosen from hydrocarbon-based oils comprising more than 6 carbon atoms, such as liquid paraffin or mineral oil; liquid petroleum jelly (liquid or pasty petrolatum); esters of C1-C26 aliphatic mono acids and of C1-C26 aliphatic monoalcohols, these esters having a total number of carbon atoms of greater than or equal to 10, in particular isopropyl myristate and isononyl isononanoate; fatty alcohols such as octyldodecanol; plant oils, in particular avocado oil, camellia oil and olive oil; and mixtures thereof.

Preferably, the fatty substance(s) according to the invention are non-silicone.

They are preferably chosen from liquid fatty substances that are not alkoxylated or more specifically, not oxyalkylenated or glycerolated.

Preferably, the fatty substance(s) according to the invention are chosen from mineral oil, liquid petrolatum or liquid petroleum jelly, and mixtures thereof.

Preferably, the content of non-alkoxylated fatty substances that are liquid at room temperature in the compositions of the present invention ranges from about 1 to about 60% by weight and preferably in an amount ranging from about 5 to about 50% by weight, more preferably from about 5 to about 40% by weight, even more preferably from about 7 to about 30% by weight, or such as from about 15 to about 40% by weight, or such as from about 20 to about 35% by weight, based on the total weight of the composition, including all ranges and subranges therebetween.

In some embodiments, the at least one liquid fatty substance is employed in the composition of the present invention in an amount of at least about 5%, or at least about 7% by weight, or at least about 15% by weight, or at least about 20% by weight, or at least about 25% by weight, or at least about 30% by weight, or at least about 35% by weight, based on the total weight of the composition. In other embodiments, the at least one liquid fatty substance is employed in the composition of the present invention in an amount ranging from about 20 to about 50% by weight, or preferably from about 20 to about 40% by weight, or more preferably from about 20 to about 35% by weight, or even more preferably from about 20 to about 30% by weight, based on the total weight of the composition, including all ranges and subranges therebetween.

In yet other embodiments, the at least one liquid fatty substance may be employed in an amount of about 38%, or about 37%, or about 36%, or about 35%, or about 34%, or about 33%, or about 32%, or about 30%, or about 25%, or about 22%, or about 15%, or about 10%, or about 8% by weight, based on the total weight of the composition.

Alkoxylated Nonionic Surfactants

The at least one alkoxylated nonionic surfactant of the present invention may be chosen, for example, from polyethoxylated and/or polypropoxylated alkyl phenols, alpha-diols and alcohols, comprising fatty chains comprising, for example, from 8 to 18 carbon atoms, and the number of ethylene oxide and/or propylene oxide groups may range from 2 to 50. The at least one non-ionic surfactant may be chosen, for example, from copolymers of ethylene oxide and of propylene oxide, condensates of ethylene oxide and/or of propylene oxide with fatty alcohols; polyethoxylated fatty amides comprising, for example, from 2 to 30 moles of ethylene oxide, polyglycerolated fatty amides comprising on average 1 to 5, and, for example, 1.5 to 4, glycerol groups; polyethoxylated fatty amines comprising, for example, from 2 to 30 moles of ethylene oxide; oxyethylenated fatty acid esters of sorbitan (ethoxylated sorbitan esters) comprising, for example, from 2 to 30 moles of ethylene oxide, and mixtures thereof.

In certain embodiments, the at least one alkoxylated nonionic surfactant of the present invention is selected from oxyethylenated nonionic surfactants. Oxyethylenated nonionic surfactants may be chosen from alkoxylated fatty alcohols such as oxyethylenated fatty alcohols, polyoxyethylenated esters of saturated or unsaturated, linear or branched, C8-C30 acids and of sorbitol, and mixtures thereof.

In certain embodiments, the at least one alkoxylated nonionic surfactant of the present invention is chosen from one or more oxyethylenated fatty alcohols with a number of oxyethylene units of greater than or equal to 10.

Preferably, such a fatty alcohol comprises from 12 to 30 carbon atoms, more preferably 14 to 24 carbon atoms and better still from 16 to 22 carbon atoms.

The number of oxyethylene units is preferably greater than or equal to 15.

Preferred compounds are oxyethylenated lauryl, cetyl and stearyl alcohols, comprising at least 10, preferably at least 15 and better still at least 20 oxyethylene units.

Preferably, the maximum number of oxyethylene units is 200 and better still 100.

Compounds corresponding to this definition are especially known under the following INCI names: Steareth-20 (stearyl alcohol containing 20 oxyethylene units), Ceteareth-25 (mixture of cetyl and stearyl alcohols containing 25 oxyethylene units), and Laureth-23 (lauryl alcohol containing 23 oxyethylene units).

Similarly, the least one alkoxylated nonionic surfactant of the present invention is chosen from one or more of oxyethylenated fatty alcohols with a number of oxyethylene units of less than 10.

Preferably, such a fatty alcohol comprises from 12 to 30 carbon atoms, more preferably 14 to 24 carbon atoms and better still from 16 to 22 carbon atoms.

The number of oxyethylene units is preferably less than or equal to 5.

The number of ethylene oxide units is greater than or equal to 1 and preferably greater than or equal to 2.

Preferred compounds are oxyethylenated cetyl and stearyl alcohols, comprising less than 5 oxyethylene units.

A particularly preferred compound corresponds to the INCI name Steareth-2 (stearyl alcohol containing 2 oxyethylene units).

Particularly preferred alkoxylated nonionic surfactants for use in the compositions of the present invention are laureth-23, steareth-20, ceteareth-25, polysorbate 60, laureth-2, steareth-2, and mixtures thereof.

In some embodiments, the at least one alkoxylated nonionic surfactant is selected from ethoxylated sorbitan esters, commercially sold under the series tradename of TWEEN by the company Croda. One example is polysorbate 60, also known as TWEEN 60 and commercially available from Croda, or also known by the series tradenames of POLAWAX or CROMUL from Croda when polysorbate is combined with a fatty alcohol, In other embodiments, the at least one alkoxylated nonionic surfactant comprises cetearyl alcohol and polysorbate 60, known by the tradename of POLAWAX NF-PA or CROMUL EM3398-PA.

The content of the at least one alkoxylated nonionic surfactant in the compositions of the present invention is at least 0.1% by weight, or ranges from about 0.1% to about 30% by weight, preferably from about 0.5% to about 20% by weight, more preferably from about 0.5% to about 10% by weight, even more preferably from about 0.75% to about 5% by weight, based on the total weight of the composition, including all ranges and subranges therebetween.

In certain embodiments, the at least one alkoxylated nonionic surfactant in the compositions of the present invention is employed in an amount of from 0.75% to about 2% by weight, based on the total weight of the composition, including all ranges and subranges therebetween.

In some embodiments, the content of the at least one alkoxylated nonionic surfactant in the compositions of the present invention is at least 0.1% by weight, and can be employed in an amount of about 0.1%, 0.2%, 0.3%, 0.4%, 0.5%, 0.6%, 0.75%, 0.8%, 0.9%, 1%, 1.1%, 1.2%, 1.3%, 1.4%, 1.5%, 1.6%, 1.7%, 1.8%, 1.9%, 2.0%, 2.1%, 2.2% by weight, based on the total weight of the composition.

In preferred embodiments, the at least one alkoxylated nonionic surfactant of the present invention is selected from laureth-23, polysorbate 60, and mixtures thereof.

Fatty Alcohols

The at least one fatty alcohol that may be employed in the composition/agent of the present invention is solid at room temperature (e.g., 25° C.) and at atmospheric pressure (760 mmHg).

According to the present invention, the term "fatty alcohol" denotes a compound of formula R—OH in which R denotes a linear or branched, saturated or unsaturated hydrocarbon-based group (i.e. a group consisting of carbon and hydrogen atoms) comprising from 8 to 40 carbon atoms.

In certain embodiments, the at least one fatty alcohol that is solid at room temperature is a non-alkoxylated fatty alcohols, specifically, a non-oxyethylenated fatty alcohol.

Preferably, such a fatty alcohol comprises from 14 to 30 carbon atoms and more preferably from 16 to 24 carbon atoms.

Fatty alcohols corresponding to this definition are especially cetyl alcohol, cetearyl alcohol, stearyl alcohol, behenyl alcohol, and mixtures thereof.

Preferably, the at least one fatty alcohol that is solid at room temperature is selected from cetyl alcohol, cetearyl alcohol, and mixtures thereof.

The content of the at least one fatty alcohol that is solid at room temperature and selected from non-oxyethylenated fatty alcohols that are solid at room temperature is advantageously at least 0.1% by weight based on the total weight of the composition, or ranges from 0.1% to 30% by weight, preferably, from 0.5% to 20% by weight, more preferably from 0.5% to 15% by weight, even more preferably from about 0.75% to about 10% by weight, based on the total weight of the composition, including all ranges and subranges therebetween.

In certain embodiments, the at least one fatty alcohol that is solid at room temperature and selected from non-oxyethylenated fatty alcohols that are solid at room temperature is employed in the compositions of the present invention in an amount of from 5% to about 10% by weight, based on the total weight of the composition, including all ranges and subranges therebetween.

In some embodiments, the content of the at least one fatty alcohol that is solid at room temperature and selected from non-oxyethylenated fatty alcohols that are solid at room temperature is advantageously at least 0.1% by weight based on the total weight of the composition, or is present in an amount of about 0.5%, 0.75%, 0.95%, 1%, 1.5%, 2%, 2.5%, 3%, 3.5%, 4%, 4.5%, 5%, 5.5%, 6%, 6.5%, 7%, 7.5%, 8%, 8.5%, 8.8%, 9.75%% by weight, based on the total weight of the composition based on the total weight of the composition.

Auxiliary Ingredients

The compositions according to the invention may also comprise any auxiliary ingredient usually used in the field under consideration, selected, for example, from rheology modifiers, thickening/viscosity-modifying agents, surfactants such as anionic surfactants, amphoteric or zwitterionic surfactants, cationic surfactants and nonionic surfactants chosen from alkylpolyglycosides, N-alkylglucamine derivatives, amine oxides such as (C10-C14)alkyl amine oxides and N-acylaminopropylmorpholine oxides, shine agents, fillers, colorants, pigments, chelating agents, sequestering agents, fragrances, preservatives, stabilizers, and mixtures thereof.

It is a matter of routine operations for a person skilled in the art to adjust the nature and amount of the additives present in the compositions in accordance with the invention such that the desired cosmetic properties and stability properties thereof are not thereby affected.

If present in the composition of the invention, these auxiliary ingredients may constitute from about 0.5% to about 30%, typically from about 1% to about 15% and more typically, from about 1% to about 10% by weight, based on the total weight of the composition, including all ranges and subranges therebetween.

The compositions of the present invention may comprise stabilizers, for example sodium chloride, magnesium dichloride or magnesium sulfate.

The rheology modifiers and thickening/viscosity-modifying agents that may be employed in compositions of the present invention may include any water-soluble or water-dispersible compound that is compatible with the compositions of the invention, such as acrylic polymers, non-acrylic polymers, starch, cellulose-based polymers, non-polymeric and polymeric gelling agents, silica particles, clay, and mixtures thereof.

The surfactants that may be employed in the compositions of the present invention can be chosen from one or the combination of two or more of the following: anionic surfactants, amphoteric or zwitterionic surfactants, cationic surfactants and nonionic surfactants chosen from alkylpolyglycosides, N-alkylglucamine derivatives, amine oxides such as (C10-C14)alkyl amine oxides and N-acylaminopropylmorpholine oxides, and mixtures thereof. These surfactants may be present in compositions of the present invention in an amount ranging from about 0.01 to about 40%, such as from 0.05 to 30% by weight, or from about 0.1 to about 20% by weight, or from about 0.1 to about 15% by weight, based on the total weight of the compositions, including all ranges and subranges therebetween.

Anionic Surfactants

The term "anionic surfactant" is understood to mean a surfactant comprising, as ionic or ionizable groups, only anionic groups. These anionic groups are preferably chosen from the following groups: CO2H, CO2-, SO3H, SO3-, OSO3H, OSO3-, H2PO3, —HPO3-, —PO32-, —H2PO2, =HPO2, —HPO2-, =PO2-, =POH and =PO—.

Mention may be made, among the anionic surfactants capable of being used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, acyl sarcosinates, acyl glutamates, alykyl ether carboxylates, alkyl sulfosuccinamates, acyl isethionates and N-acyl taurates; monoalkyl esters of polyglycoside-polycarboxylic acids, acyl lactylates, salts of D-galactosideuronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds can be oxyethylenated and then preferably comprise from 1 to 50 ethylene oxide units and better still from 1 to 10 ethylene oxide units.

The salts of C6-C24 alkyl monoesters of polyglycoside-polycarboxylic acids can be chosen from C6-C24 alkyl polyglycoside-citrates, C6-C24 alkyl polyglycoside-tartrates and C6-C24 alkyl polyglycoside-sulfosuccinates.

The acyl lactylates preferably have an acyl group comprising from 8 to 20 carbon atoms.

When the anionic surfactant is in the salt form, it can be chosen from the alkali metal salts, such as the sodium salt or potassium salt, the ammonium salt, the amine salts and in particular the aminoalcohol salts, or the alkaline earth metal salts, such as the magnesium salt.

Use is preferably made of alkali metal or alkaline earth metal salts and in particular of sodium or magnesium salts.

The preferred anionic surfactants are chosen from (C6-24)alkyl sulfates, (C6-24)alkyl ether sulfates, acyl glutamates and (C6-C24)alkyl ether carboxylates, in particular in the form of alkali metal, ammonium, aminoalcohol or alkaline earth metal salts, or a mixture of these compounds.

In particular, use is preferably made of (C12-20)alkyl sulfates, (C12-20)alkyl ether sulfates comprising from 2 to 20 ethylene oxide units, acyl glutamates or (C12-C20)alkyl ether carboxylates, in particular in the form of alkali metal, ammonium, aminoalcohol and alkaline earth metal salts, or a mixture of these compounds.

Amphoteric or Zwitterionic Surfactants

The amphoteric or zwitterionic surfactants can in particular be derivatives of optionally quaternized secondary or tertiary aliphatic amines comprising at least one anionic group, such as, for example, a carboxylate, sulfonate, sulfate, phosphate or phosphonate group, and in which the aliphatic group or at least one of the aliphatic groups is a linear or branched chain comprising from 8 to 22 carbon atoms.

Mention may in particular be made of (C8-C20)alkyl betaines, sulfobetaines, (C8-C20)alkylamido(C1-C6)alkyl betaines, such as cocoamidopropyl betaine, or (C8-C20) alkylamido(C1-C6)alkyl sulfobetaines.

Mention may also be made of optionally quaternized secondary or tertiary aliphatic amines such as disodium cocoamphodiacetate, disodium lauroamphodiacetate, disodium caprylamphodiacetate, disodium caprylamphodiacetate, disodium cocoamphodi-propionate, disodium lauroamphodipropionate, disodium caprylamphodipropio-nate, disodium caprylamphodipropionate, lauroamphodipropionic acid and co-coampho-dipropionic acid.

Mention may be made, by way of example, of the cocoamphodiacetate sold by Rhodia under the trade name Miranol® C2M Concentrate.

Mention may also be made of the compound under the name sodium diethylaminopropyl cocoaspartamide and sold by Chimex under the name Chimexane HB.

Preferably, the amphoteric or zwitterionic surfactants are chosen from (C8-C20)alkyl betaines, (C8-C20)alkylamido (C1-C6)alkyl betaines and (C8-C20)alkylamphodiacetates, and also the sodium salt of diethylaminopropyl laurylaminosuccinamate, and their mixtures.

Preferably, the amphoteric or zwitterionic surfactants are chosen, alone or as a mixture, from cocamidopropyl betaine, coco-betaine and cocoamphodiacetate.

Cationic Surfactants

The at least one cationic surfactant may be chosen, for example, from: salts of optionally polyoxyalkylenated primary, secondary and tertiary fatty amines; quaternary ammonium salts such as tetra alkyl ammonium, alkylamidoalkyltrialkyl ammonium, trialkylbenzyl ammonium, trialkylhydroxyalkyl ammonium and alkylpyridinium chlorides and bromides; imidazoline derivatives; and cationic amine oxides.

Agents and Hair Treatment Compositions for Shaping or Altering the Shape of Hair According the present invention, the agent for shaping or altering the shape of hair comprises a hair treatment composition containing an alkaline material selected from hydroxide-containing compounds and carbonate compounds, a cationic polymer selected from at least one quaternary diammonium polycondensate, amphoteric polymer selected from at least one quaternary ammonium compound, an organic solvent, and water, wherein the weight ratio of (b) to (c) ranges from about 1 up to about 3. Optionally, said agent can further comprise an activator component. In certain embodiments, the activator component comprises: (i) at least one hydroxide-containing compound or at least one carbonate compound, and optionally, (ii) a solvent.

In certain embodiments, the amount of the solvent in the activator component is in an amount of at least about 50% by weight, or of about 60% by weight, or of about 70% by weight, or of about 75% by weight, or of about 80% by weight, based on the weight of the activator component.

In other embodiments, the activator component is essentially free of water and is in powder form.

The agent for shaping or altering the shape of hair may comprise a one-component system ("no mix" system) or a two-component system ("mix" system). In a no mix system, the activator component of the present invention is not employed in the agent for shaping or altering the shape of hair. In a mix system, the activator component of the present invention is employed in said agent.

Thus, in one embodiment, the agent for shaping or altering the shape of hair is a no mix system wherein the alkaline material in the hair treatment composition is at least one hydroxide-containing compound selected from alkali metal hydroxides, alkaline-earth metal hydroxides, transition metal hydroxides, and mixtures thereof and the alkaline material is not selected from a carbonate compound. In said no mix system, the activator component is not employed or required.

In another embodiment, the agent for shaping or altering the shape of hair is a mix system ("mix system I") wherein the alkaline material in the hair treatment composition is at least one carbonate compound selected from lithium carbonate, sodium carbonate, potassium carbonate, guanidine carbonate, and mixtures thereof and the alkaline material is not selected from a hydroxide-containing compound. Preferably, the carbonate compound is selected from guanidine carbonate. In said mix system I, the activator component is employed and comprises at least one hydroxide-containing compound selected from alkali metal hydroxides, alkaline-earth metal hydroxides, transition metal hydroxides, and mixtures thereof. Preferably, the hydroxide-containing compound of the activator component is calcium hydroxide.

In yet another embodiment, the agent for shaping or altering the shape of hair is a mix system ("mix system II") wherein the alkaline material in the hair treatment composition is at least one hydroxide-containing compound selected from alkali metal hydroxides, alkaline-earth metal hydroxides, transition metal hydroxides, and mixtures thereof. Preferably, the hydroxide-containing compound of the activator component is calcium hydroxide. In said mix system II, the activator component is employed and comprises at least one carbonate compound selected from lithium carbonate, sodium carbonate, potassium carbonate, guanidine carbonate, and mixtures thereof and the alkaline material is not selected from a hydroxide-containing compound. Preferably, the carbonate compound is selected from guanidine carbonate.

In both mix systems I and II, the hair treatment composition is capable of being combined with the activator component, resulting in the formation of a mixture or composition (also called ready to use composition) which is applied onto hair. The combination of the hair treatment compositions and the activator component results in the formation of guanidine hydroxide due to the reaction between the alkaline material in the hair treatment compositions and the hydroxide-containing compound or the carbonate compound in the activator component. The guanidine hydroxide serves as the active material for straightening or relaxing hair.

In preferred embodiments of the present invention, the agent for shaping or altering the shape of hair comprising the hair treatment composition or the combination of the hair treatment composition and the activator component is a composition for straightening or relaxing hair.

The activator component may be separately packaged from the hair treatment composition of the invention and mixed with said composition right before use on hair in order to shape or alter the shape of hair, for example, by straightening or relaxing the hair.

The activator component of the present invention may be mixed with varying amounts of the hair treatment composition of the present invention to obtain a ready to use composition with properties suitable for a particular use or to suit different types of hair and/or to achieve different degrees of hair relaxation or straightening In some embodiments, the activator component is combined with the hair treatment composition in a weight ratio of from about 10:1 to about 1:10, or from about 1:3 to about 1:10, or from about 3:1 to about 1:10, or from about 1:3 to about 1:5, or from about 3:1 to about 1:5, or at about 1:3, or at about 1:4, in order to form a ready to use composition.

The term "combined" and all variations of this term as used herein refers to contacting or mixing or reconstituting or dissolving or dispersing or blending or shaking the activator component with the hair treatment composition. It can also mean introducing the activator component to the hair treatment composition. It may also mean placing the activator component in the same vessel or container as the hair treatment composition.

The step of contacting the activator component composition with the hair treatment composition can be conducted in any vessel suitable for holding the resulting ready to use composition.

The term "ready to use composition" as used herein refers to the composition resulting from mixing the activator component and the hair treatment composition of the invention. Generally, the ready to use composition is to be prepared by the consumer or hair dresser on the day that the hair is to be straightened or relaxed. It can be applied onto hair immediately after it is prepared. There could also be a certain period of time before the ready to use composition is applied onto hair from the time of preparation of said composition, such as from between about 2 minutes to about 60 minutes, or such as from between about 2 minutes to about 30 minutes.

pH

In accordance with the present invention, the pH of the hair treatment compositions or the agent for shaping or altering the shape of hair or the composition resulting from the combination of the hair treatment composition and the activator component (ready to use composition) is equal to or greater than 12 or is equal to or greater than 13, and can range from about 12.5 to about 14, or preferably from about 13 to about 14, or more preferably from about 13.2 to about 13.8, or even more preferably from about 13.5 to about 13.7, including all ranges and subranges therebetween.

In certain embodiments, the pH of the compositions, agents and ready to use compositions of the present invention is at about 12, 12.1, 12.2, 12.3, 12.4, 12.5, 12.8, 13, 13.1, 13.2, 13.3, 13.4, 13.5, 13.6, 13.7, 13.8, 13.9, and 14.

The pH of the hair treatment composition or agents of the present invention may be adjusted to the desired value using conventional acidifying or basifying agents.

The pH of all numbers expressing pH values are to be understood as being modified in all instances by the term "about" which encompasses up to +/−1% of the indicated pH value (e.g. "about 12.2" means 12.125-12.32% and "about 2%" means 1.8%-2.2%).

Ratios

In some embodiments, the weight ratio of the at least one cationic polymer selected from at least one quaternary diammonium polycondensate to the at least one amphoteric polymer selected from quaternary ammonium compounds in the compositions of the present invention is equal to or greater than about 1.

In other embodiments, the weight ratio of the at least one cationic polymer selected from at least one quaternary diammonium polycondensate to the at least one amphoteric polymer selected from quaternary ammonium compounds is equal to or greater than about 1, or from equal to or greater than about 1 to about 3, preferably from about 1 to about 2.5, or more preferably from about 1 to about 2, including all ranges and subranges therebetween.

In yet other embodiments, the weight ratio of the at least one cationic polymer selected from at least one quaternary diammonium polycondensate to the at least one amphoteric polymer selected from quaternary ammonium compounds is about 1, about 1.1, about, 1.2, about 1.3, about 1.4, about 1.5, about 1.6, about 1.7, about 1.8, about 1.9, about 2, about 2.1, about 2.2, about 2.3, about 2.4, or about 2.5.

In an embodiment, the present invention relates to an agent for relaxing or straightening hair, the agent comprising:

A. A hair treatment composition containing:
  (a) from about 1 to about 20% by weight of at least one alkaline material at least one alkaline material selected from:
    (i) at least one hydroxide-containing compound selected from alkali metal hydroxides, alkaline-earth metal hydroxides, transition metal hydroxides, and mixtures thereof; and
    (ii) at least one carbonate compound selected from lithium carbonate, sodium carbonate, potassium carbonate, guanidine carbonate, and mixtures;
  (b) from about 0.1% to about 5% by weight of at least one cationic polymer selected from at least one quaternary diammonium polycondensate composed of repeat units corresponding to the formula (a) below:

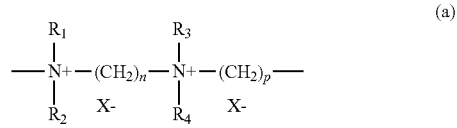

(a)

in which R1, R2, R3 and R4, which are identical or different, denote an alkyl or hydroxyalkyl group having from 1 to 4 carbon atoms, n and p are integers that vary from 2 to 6 and X— is a mineral or organic acid anion;
  (c) from about 0.1% to about 5% by weight of at least one amphoteric polymer selected from the copolymer of diallyldimethylammonium chloride and acrylic acid, the terpolymer of diallyldimethylammonium chloride, acrylic acid, and acrylamide, the terpolymer of acrylic acid, methyl acrylate and methacrylamidopropyltrimethyl ammonium chloride, the terpolymer of methacrylamidopropyltrimethyl ammonium chloride (MAPTAC), acrylamide, and acrylic acid, and mixtures thereof;
  (d) at least one organic solvent selected from C1-C4 lower alcohols, glycols, polyols, polyol ethers, and mixtures thereof; and
  (e) water;
  all weights above being based on the total weight of the composition;
  wherein the pH of the composition is from about 13.2 to about 13.8;
  wherein the weight ratio of (b) to (c) ranges from about 1 to about 2.5. and optionally,
B. an activator component comprising: (i) at least one hydroxide-containing compound or at least one carbonate compound; and (ii) optionally, a solvent.

The above-described hair treatment composition may further comprise at least one non-alkoxylated fatty substance that is liquid at room temperature and selected from C6-C16 hydrocarbons, hydrocarbons containing more than 16 carbon atoms, non-silicone oils of plant, mineral or synthetic origin, plant oils of triglyceride type, synthetic triglycerides, fluoro oils, liquid fatty alcohols, liquid fatty acids and liquid esters of a fatty acid and/or of a fatty alcohol other than triglycerides, silicones, and mixtures thereof and present in an amount of from about 7 to about 30% by weight, or such as from about 15 to about 40% by weight, or such as from about 20 to about 35% by weight, based on the total weight of the composition, including all ranges and subranges therebetween.

The above-described hair treatment composition may also further comprise at least one alkoxylated nonionic surfactant selected from oxyethylenated fatty alcohols, oxyethylenated fatty acid esters of sorbitan, and mixtures thereof and present in an amount of from about 0.5% to about 10% by weight, even more preferably from about 0.75% to about 5% by weight, based on the total weight of the composition, including all ranges and subranges therebetween.

The above-described hair treatment composition may also further comprise at least one fatty alcohol that is solid at room temperature and selected from cetyl alcohol, cetearyl alcohol, stearyl alcohol, behenyl alcohol, and mixtures thereof and present in an amount of from about 0.5% to about 15% by weight, even more preferably from about 0.75% to about 10% by weight, based on the total weight of the composition, including all ranges and subranges therebetween.

In certain embodiments, when the activator component is not employed, the amounts of the ingredients in the above-described hair treatment compositions are equivalent to the amounts of said ingredients in the agent for relaxing or straightening hair.

The hair treatment compositions of the present invention may be in the form of a liquid, a gel, a lotion, or a cream; it can also be an emulsion, preferably, an oil-in-water emulsion.

In preferred embodiments, the agent for shaping or altering the shape of hair is a hair relaxing or straightening composition.

In other preferred embodiments, the hair treatment composition of the present invention is a hair relaxing or straightening composition.

The hair treatment composition of the present invention is stable such that the activity or efficacy of the alkaline material is preserved until the composition is ready to be used.

In addition, the hair treatment composition of the present invention is stable over time; it can be stored for several months without modification.

The hair treatment composition may be packaged in any suitable container. It may also be packaged as one unit or as part of a multi-compartment kit which may additionally contain a second unit containing the activator component of the present invention, and/or a third unit containing a composition comprising a cleansing agent and/or a conditioning agent.

Without being bound to any one theory, it is believed that the at least one amphoteric polymer selected from at least one quaternary ammonium compound of the present invention, for example polyquaternium-22, imparts a conditioning benefit to the surface of hair while, the at least one cationic polymer selected from at least one quaternary diammonium polycondensate of the present invention, for example, hexadimethrine chloride, repairs and smoothens the surface of hair.

Surprisingly and unexpectedly, it was found that the combination of the at least one amphoteric polymer selected from at least one quaternary ammonium compound and the at least one cationic polymer selected from at least one quaternary diammonium polycondensate in the highly alkaline composition of the invention resulted in significantly better detangling benefits, conditioning and smoothness of the treated hair, despite the presence of the alkaline material in the composition.

It was also surprisingly and unexpectedly found that the at least one amphoteric polymer selected from at least one quaternary ammonium compound and the at least one cationic polymer selected from at least one quaternary diammonium polycondensate did not degrade or breakdown in the highly alkaline hair treatment compositions and agents for shaping or altering the shape of hair of the invention, thereby resulting in compositions that retained their hair straightening/relaxing efficacy while at the same time, imparting conditioning and smoothing benefits to the hair.

Process of Making

In an embodiment, the method of making the agents and compositions of the present invention comprises the steps of:
(1) combining:
  (a) at least one alkaline material comprising at least one hydroxide-containing compound selected from:
    (i) at least one hydroxide-containing compound selected from alkali metal hydroxides, alkaline-earth metal hydroxides, transition metal hydroxides, and mixtures thereof; and
    (ii) at least one carbonate compound selected from lithium carbonate, sodium carbonate, potassium carbonate, guanidine carbonate, and mixtures thereof;
  (b) at least one cationic polymer selected from at least one quaternary diammonium polycondensate composed of repeat units corresponding to the formula (a) below:

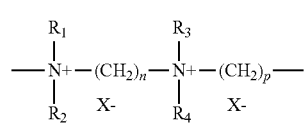

in which R1, R2, R3 and R4, which are identical or different, denote an alkyl or hydroxyalkyl group having from 1 to 4 carbon atoms, n and p are integers that vary from 2 to 6 and X— is a mineral or organic acid anion;
  (c) at least one amphoteric polymer selected from at least one quaternary ammonium compound;
  (d) at least one organic solvent; and
  (e) water; and
(2) mixing (a) to (e) in order to form a hair treatment composition having a pH equal to or greater than about 12;
wherein the weight ratio of (b) to (c) ranges from about 1 up to about 3.

Process of Relaxing or Straightening Hair

The invention also concerns a process of shaping or altering the shape of hair, for example, by straightening hair. The process comprises the steps of:
(1) contacting hair with a shampoo having a neutral pH;
(2) rinsing the hair with water;
(3) providing a hair treatment agent for shaping or altering the shape of hair, the hair treatment agent comprising:
A. a composition containing:
  (a) at least one alkaline material selected from:
    (i) at least one hydroxide-containing compound selected from alkali metal hydroxides, alkaline-earth metal hydroxides, transition metal hydroxides, and mixtures thereof; and
    (ii) at least one carbonate compound selected from lithium carbonate, sodium carbonate, potassium carbonate, guanidine carbonate, and mixtures thereof;
  (b) at least one cationic polymer selected from at least one quaternary diammonium polycondensate composed of repeat units corresponding to the formula (a) below:

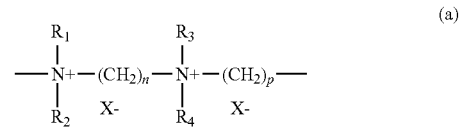

in which R1, R2, R3 and R4, which are identical or different, denote an alkyl or hydroxyalkyl group having from 1 to 4 carbon atoms, n and p are integers that vary from 2 to 6 and X— is a mineral or organic acid anion;
  (c) at least one amphoteric polymer selected from at least one quaternary ammonium compound;
  (d) at least one organic solvent; and
  (e) water;
  all weights above being based on the total weight of the composition; wherein the weight ratio of (b) to (c) is equal to or greater than 1 up to about 3; and optionally,
B. an activator component; and
wherein the agent has a pH equal to or greater than about 12;
(4) applying composition A onto the hair, or mixing composition A with the activator component in B to form a mixture or a ready-to-use composition, then applying the mixture onto the hair;
(5) brushing the hair;
(6) heating the hair at a temperature of at least 40° C., preferably at a temperature of from about 40° C. to about 250° C., preferably from about 100° C. to about 230° C., or more preferably from about 150° C. to about 230° C.; while optionally applying a smoothing action on the hair, wherein when a smoothing action is employed, the heating action and smoothing action are accomplished by use of a heating flat iron device; and (7) rinsing the hair with water or contacting the hair with an intermediate agent having a neutral pH and selected from a shampoo and/or a conditioner, followed by rinsing with water.

In certain embodiments, the intermediate agent in the process above is a shampoo or conditioner, preferably having a neutral pH.

In certain embodiments, the composition is allowed to remain (leave-on time) on the keratin fibers, for example, from about 1 to about 60 minutes, or such as from about 5 to about 45 minutes, or such as from about 5 to about 30 minutes, or such as from about 10 to about 20 minutes, or such as at about 20 minutes, or such as at about 10 minutes.

Suitable devices for brushing or smoothing the hair include a hair brush, comb, or heating flat iron. The smoothing action on the hair may also include running the fingers through the hair.

A suitable applicator device is an applicator brush.

Heat (at a temperature of at least 40° C.) can be applied to the hair while the smoothing action is performed on the hair. The heat source can be chosen from a blow dryer, a flat iron, a hair dryer, a heat lamp, a heat wand, or other similar devices.

In addition, independently of the embodiment use, the composition or agent present on the fibers or hair is left in place for a time, generally, from about 1 to about 60 minutes, such as from about 5 to about 45 minutes, or such as from about 5 to about 20 minutes, or such as from about 10 to about 20 minutes, or such as of about 20 minutes or such as of about 10 minutes.

It has been surprisingly and unexpectedly discovered that the combination of an alkaline material comprising hydroxide-containing compounds or carbonate compounds, a cationic polymer selected from at least one quaternary diammonium polycondensate, an amphoteric polymer selected from at least one quaternary ammonium compound, an organic solvent, and water; wherein the pH of the composition is equal to or greater than 12 and wherein the weight ratio of (b) to (c) ranges from about 1 up to about 3, and optionally, an activator component comprising hydroxide-containing compounds or carbonate compounds produces a final mixture or a composition with a non-drip consistency that is still easy to spread on keratin fibers, e.g., hair, while satisfactorily shaping or altering the shape of hair such as by straightening or relaxing the hair.

The relaxing or straightening effects obtained using the compositions and processes of the present disclosure may also be durable or long lasting.

The degree of straightening or relaxing the hair may be evaluated by visually assessing the reduction in curliness and/or waviness and/or frizziness of the hair after contacting the hair with the composition of the invention. Another type of evaluation can also involve measuring the length of the hair as well as the width of the bulk of hair before and after contacting the hair with the composition of the present invention.

It was surprisingly and unexpectedly discovered that the hair contacted with the compositions of the invention did not feel rough and visually appeared to be smooth, extended and straight.

As used herein, the method and composition disclosed herein may be used on the hair that has not been artificially dyed, pigmented or permed.

As used herein, the method and composition disclosed herein may be also used on the hair that has been artificially dyed, pigmented or permed.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result.

EXAMPLES

The following Examples are intended to be non-restrictive and explanatory only, with the scope of the invention being defined by the claims.

The ingredient amounts in the compositions/formulas described below are expressed in % by weight, based on the total weight of the composition/formula.

Example 1

Compositions

TABLE 1

Inventive Compositions

| Ingredients/INCI names | Formulas % by weight of ingredient | | |
|---|---|---|---|
| | 1 | 2 | 3 |
| SODIUM HYDROXIDE | 2.2 | 2.2 | 2.2 |
| MINERAL OIL | 22 | 22 | 22 |
| PETROLATUM | 10 | 10 | 10 |
| CETYL ALCOHOL | 1 | 1 | 1 |
| HEXADIMETHRINE CHLORIDE, 60% BY WT IN WATER (MEXOMERE PO[1]) | 0.42 | 0.83 | 0.83 |
| POLYQUATERNIUM-22, 41% BY WT IN WATER (MERQUAT 280 NP POLYMER[2]) | 0.62 | 0.62 | 0.62 |
| PROPYLENE GLYCOL | 1.5 | 1.5 | 1.5 |
| LAURETH-23 | 0.75 | 0.75 | 0.75 |
| COCAMIDOPROPYL BETAINE[3], 38% BY WT IN WATER | 0.5 | 0.5 | 0.5 |
| CETEARYL ALCOHOL, 80% BY WT (and) POLYSORBATE 60, 20% BY WT (POLAWAX NF-PA-(RB), CRODA) | 11 | 11 | 11 |
| FRAGRANCE | | | 0.1 |
| WATER | QS 100 | QS 100 | QS 100 |

[1]also known under the tradename IONENE G
[2]commercially available from Nalco (Lubrizol)
[3]commercially available as MACKAM 50-ULB from Rhodia Solvay or as DEHYTON PK 45 from Cognis (BASF)

The compositions in Table 1 were prepared according to the protocol:

1. Charge mixing tank with mineral oil. Begin heating to 75° C.
2. Add petrolatum, cetearyl alcohol and polysorbate 60, laureth-23, and cetyl alcohol while heating.
3. At 75° C. add water, propylene glycol and cocamidopropyl betaine. Mix for 20 minutes.
4. Begin cooling to 40° C. and turbine for 5 minutes
5. Pre-mix sodium hydroxide with water (2%) and add to batch at 30° C. Continue to mix for 15 minutes.
6. Pre-mix hexadimethrine chloride and polyquaternium-22 with water (about 1.5%) and add to batch at 30° C.
7. Add fragrance to batch at 30° C. Turbine for 5 minutes.
8. Batch is ready for analysis at 25° C.

TABLE 2

Comparative compositions

| Ingredients/INCI names | Formulas % by weight of ingredient | | | | | | | | | |
|---|---|---|---|---|---|---|---|---|---|---|
| | C1 | C2 | C3 | C4 | C5 | C6 | C7 | C8 | C9 | C10 |
| SODIUM HYDROXIDE | 2.2 | 2.2 | 2.2 | 2.2 | 2.2 | 2.2 | 2.2 | 2.2 | 2.2 | 2.1 |
| MINERAL OIL | 22 | | 22 | 22 | 22 | 22 | 22 | 22 | 22 | 18 |
| CETEARYL ALCOHOL | | | | 9 | | | | | | |
| PETROLATUM | 10 | | 10 | 10 | 10 | 10 | 10 | 10 | 10 | 12.5 |
| CETYL ALCOHOL | 1 | 0.5 | 1 | 1 | 1 | 1 | 1 | 1 | 0.5 | 1.25 |
| MINERAL OIL, 65% BY WT (and) PARAFFIN, 21% BY WT (and) MICROCRYSTALLINE WAX, 14% BY WT (ASTRA 50/WHITE PETROLEUM JELLY[7]) | | 10 | | | | | | | | |
| MINERAL OIL | | 22 | | | | | | | | |
| FRAGRANCE | | 0.125 | | | | | | | | |
| HEXADIMETHRINE CHLORIDE, 60% BY WT IN WATER (Mexomere PO[1]) | 0.83 | | 0.42 | 0.83 | | 0.83 | | | 0.83 | |
| POLYQUATERNIUM-22, 41% BY WT IN WATER (MERQUAT 280 NP POLYMER[2]) | | | | | | | | 1.23 | | |
| POLYQUATERNIUM-22, 37.5% BY WT IN WATER (MERQUAT 295 POLYMER[5]) | | | 0.67 | | | | | | | |
| POLYQUATERNIUM-6, 40% BY WT IN WATER (MERQUAT 100 POLYMER[6]) | | | | | | 1.25 | 0.63 | | | |
| PROPYLENE GLYCOL | 1.5 | 2 | 1.5 | 1 | 1.5 | 1.5 | 1.5 | 1.5 | 2 | 1 |
| POLYSORBATE 60 | | | | 2 | | | | | | |
| LAURETH-23 | 0.75 | | 0.75 | 0.75 | 0.75 | 0.75 | 0.75 | 0.75 | | 1 |
| COCAMIDOPROPYL BETAINE[4], 30% BY WT IN WATER | | 0.75 | | | | | | | | |
| COCAMIDOPROPYL BETAINE[3], 38% BY WT IN WATER | 0.5 | | 0.5 | 0.5 | 0.5 | 0.5 | 0.5 | 0.5 | 0.53 | |
| CETEARYL ALCOHOL (and) POLYSORBATE 60 | 11 | 10.5 | 11 | | 11 | 11 | 11 | 11 | 10.5 | 11 |
| PEG-75 LANOLIN | | 0.65 | | | | | | | 0.65 | |
| FRAGRANCE | | 0.125 | | | 0.1 | 0.1 | 0.1 | 0.1 | 0.125 | |
| WATER | QS 100 | QS 100 | QS 100 | QS 100 | QS 100 | QS 100 | QS 100 | QS 100 | QS 100 | QS 100 |

[4]commercially available as VELVETEX BK 35 from Cognis (BASF) or as LEXAINE C from Inolex Chemical Company
[5]commercially available from Nalco (Lubrizol)
[6]commercially available from Nalco (Lubrizol)
[7]commercially available from Akulu Marchon In comparison to the comparative compositions, the inventive compositions were preferred for product consistency (thick, cream texture), wet combing, mass effect of dry hair and wet hair smoothness in tests on hair on heads of human volunteers.

Example 2

Stability of Inventive Compositions

The inventive compositions were shown to be stable up to 8 weeks in a controlled chamber at various temperatures at 5° C., 25° C., 37° C., and 45° C. as well as 10 days in a Freeze/Thaw cycle where the pH and viscosity had small fluctuations and there was no phase separation.

Example 3

Salon Testing

The inventive and comparative compositions were tested on the hair on heads of human volunteers in half-head studies (salon test) by applying the test compositions on the hair evenly and leaving them on the hair for a period of time. The compositions were then rinsed off the hair with water. The hair was then contacted and cleansed with a neutral shampoo and rinsed well with water. The hair was styled as desired.

| SALON TEST | OBSERVED DIFFERENCES IN CERTAIN ATTRIBUTES BY PANELIST AND/OR SALON HAIR DRESSER |
|---|---|
| Formula 1 (inventive) vs Formula C9 (comparative) | The inventive composition performed better with respect to product consistency, wet hair smoothness, discipline (less frizz), and wet combing properties as compared to the comparative composition |
| Formula C1 (comparative) vs Formula 1 (inventive) | The inventive composition performed better with respect to product texture, reduced scalp sensitivity, wet combing properties and product preference as compared to the comparative composition |
| Formula 2 (inventive) vs Formula C1 (comparative) | The inventive composition performed better with respect to product texture, wet combing properties, dry hair suppleness, ease of shaping with a flat iron, and product preference as compared to the comparative composition |

| SALON TEST | OBSERVED DIFFERENCES IN CERTAIN ATTRIBUTES BY PANELIST AND/OR SALON HAIR DRESSER |
|---|---|
| Formula 3 (inventive) vs Formula C10 (comparative) | The inventive composition performed better with respect to rinsing speed, wet hair combing, and shine as compared to the comparative composition. |

Example 4

Wet Combing Experiments on Hair Swatches to Test Various Polymers

The wet combing studies were conducted on hair swatches as follows:
1. Aqueous solutions at pH 13.5 to 13.7 containing 0.5% by weight of active material of the following polymers were prepared: These solutions contained water, the test raw materials and sodium hydroxide in an amount needed to reach the desired pH of 13.5-13.7.
   a. No polymer (Control solution at same pH)
   b. Hexadimethrine chloride
   c. Polyquaternium-6
   d. Polyquaternium-7
   e. Polyquaternium-22
   f. Polyquaternium-47
   g. Hexadimethrine chloride+Polyquaternium-22
   h. Hexadimethrine chloride+Polyquaternium-6
2. Hair swatches were prepared with a length of 7 cm and weight of 0.25 grams each.
3. Hair swatches were immersed in the solutions for 15 minutes.
4. The swatches were then washed twice with 10% ALS solution.
5. The swatches were combed 20 times prior to testing.
6. Swatches were then dipped 3 times in water, with excess water removed by running the hair sample through the operator's fingertips.
7. The samples were then secured and combed with a wet combing instrument device.
8. The above procedure was repeated 10 times per swatch.

The wet combing instrument measured: (1) the peak combing force required to comb the swatch which primarily translates to the force required to detangle the hair and (2) the work of combing required to pass the comb through the swatch; when the force measured is plotted against the distance by which the comb was moved through the hair, the area under the curve corresponds to the wet combing force. This translates to the overall conditioning of the hair. FIG. 1 shows a sample combing profile.

Summary of wet combing force measurements for high pH solutions with 0.5% polymer content (taken from wet combing plots for two trials)

| | Peak Wet Combing Force Values (gmf) | Work of Wet Combing Values (gmf) |
|---|---|---|
| Trial one | | |
| Control (no polymer) | 47.86 | 9.16 |
| Hexadimethrine chloride | 9.54 | 3.31 |
| Polyquaternium-22 | 17.85 | 5.29 |
| Hexadimethrine chloride + Polyquaternium-22 | 9.71 | 3.35 |
| Polyquaternium-6 | 29.84 | 8.02 |
| Hexadimethrine chloride + Polyquaternium-6 | 41.24 | 9.88 |
| Trial two | | |
| Control (no polymer) | 44.22 | 10.65 |
| Hexadimethrine chloride | 26.40 | 7.21 |
| Polyquaternium-22 | 28.06 | 8.00 |
| Hexadimethrine chloride + Polyquaternium-22 | 29.15 | 8.70 |
| Polyquaternium-6 | 59.24 | 14.38 |
| Hexadimethrine chloride + Polyquaternium-6 | 38.69 | 10.42 |

From the results above, for trial one, it was unexpectedly and surprisingly found that the treatment of the hair with solutions containing hexadimethrine chloride alone and the combination of hexadimethrine chloride and Polyquaternium-22 resulted in greatly reduced peak combing forces and reduced wet combing forces, indicating a substantial/significant effect on the surface of the fibers. The results for the combination of hexadimethrine chloride+Polyquaternium-22 were significantly different from those obtained with the control. The forces for polyquaternium-22 alone were higher compared to those obtained for hexadimethrine chloride alone and either comparable to or greater than those obtained for the combination of hexadimethrine chloride and Polyquaternium-22. The results for another type of polyquaternium compound, polyquaternium-6 (non-amphoteric), resulted in wet combing forces that were comparable to those for the controls and higher than those obtained for hexadimethrine chloride+Polyquaternium-22 combination (invention).

It appears that the addition of polyquaternium-22 to hexadimethrine chloride did not adversely affect the wet combing performance of hexadimethrine chloride. While the measured forces on the hair treated with the solution containing the combination of hexadimethrine chloride and polyquaternium-22 could be comparable to the forces measured with the hair treated with the solutions containing hexadimethrine chloride alone and to Polyquaternium-22 alone, when formulas with hexadimethrine chloride alone were tested against the formulas containing the combination of hexadimethrine chloride and polyquaternium-22 in a salon test, there was a noticeable difference in scalp comfort wherein more scalp irritation with hexadimethrine chloride only was observed. Thus, the presence of polyquaternium-22 results in the reduction or minimization of scalp irritation attributed to the use of an alkaline solution. There were also differences observed with respect to wet combing, dry hair suppleness, ease of shaping with an iron and volunteer preference favoring the inventive formula, as well as in smoothness and tactile feel in favor of the inventive formula.

It is to be understood that the foregoing describes preferred embodiments of the invention and that modifications may be made therein without departing from the spirit or scope of the invention as set forth in the claims.

What is claimed is:

1. An agent for shaping or altering the shape of hair, the agent comprising:
   A. a hair treatment composition comprising:
      (a) at least one alkaline material selected from the group consisting of:
         (i) at least one hydroxide-containing compound selected from the group consisting of alkali metal hydroxides, alkaline-earth metal hydroxides, transition metal hydroxides, and mixtures thereof; and
         (ii) at least one carbonate compound selected from the group consisting of lithium carbonate, sodium carbonate, potassium carbonate, guanidine carbonate, and mixtures thereof;
      (b) hexadimethrine chloride;
      (c) polyquaternium-22;
      (d) at least one organic solvent; and
      (e) water;
         wherein the weight ratio of (b) to (c) ranges from 1 to about 2.4;
         wherein the pH of the hair treatment composition is equal to or greater than 12; and
         wherein the hair treatment composition is stable up to 8 weeks in a controlled chamber at 5° C., 25° C., 37° C., and 45° C., and for 10 days in a freeze/thaw cycle; and
   B. optionally an activator component;
   wherein the pH of the agent is equal to or greater than 12.

2. The agent of claim 1, wherein the at least one alkaline material (a) is selected from the (i) at least one hydroxide-containing compound and is present in an amount of from about 0.1% to about 30% by weight of the hair treatment composition.

3. The agent of claim 2, wherein the at least one hydroxide-containing compound is selected from sodium hydroxide, potassium hydroxide, lithium hydroxide, calcium hydroxide, magnesium hydroxide, barium hydroxide, strontium hydroxide, manganese hydroxide, zinc hydroxide, and mixtures thereof.

4. The agent of claim 3, wherein the at least one hydroxide-containing compound is selected from sodium hydroxide, potassium hydroxide, lithium hydroxide, calcium hydroxide, and mixtures thereof.

5. The agent of claim 4, wherein the at least one alkaline material in the hair treatment composition (A) is not selected from the (ii) at least one carbonate compound.

6. The agent of claim 4, wherein the at least one hydroxide-containing compound is calcium hydroxide.

7. The agent of claim 1, wherein the activator component (B) comprises guanidine carbonate, and optionally, a solvent.

8. The agent of claim 7, wherein the activator component (B) is capable of being combined with the hair treatment composition.

9. The agent of claim 8, wherein the agent comprises guanidine hydroxide formed from a combination of the hair treatment composition (A) with the activator component (B).

10. The agent of claim 1, wherein the at least one alkaline material in the hair treatment composition (A) is selected from the (ii) at least one carbonate compound.

11. The agent of claim 10, wherein the at least one carbonate compound is guanidine carbonate.

12. The agent of claim 11, wherein the at least one alkaline material in the hair treatment composition (A) is not selected from the (i) at least one hydroxide-containing compound.

13. The agent of claim 1, wherein the activator component (B) comprises calcium hydroxide, and optionally, a solvent.

14. The agent of claim 13, wherein the activator component (B) is capable of being combined with the hair treatment composition.

15. The agent of claim 14, wherein the agent comprises guanidine hydroxide formed from a combination of the hair treatment composition (A) with activator composition (B).

16. The agent of claim 1, wherein the at least one organic solvent is selected from the group consisting of C1-C4 lower alcohols, glycols, polyols, polyol ethers, and mixtures thereof.

17. The agent of claim 1, further comprising at least one non-alkoxylated fatty substance that is liquid at 25° C.

18. The agent of claim 17, wherein the at least one non-alkoxylated fatty substance that is liquid at 25° C. is selected from the group consisting of C6-C16 hydrocarbons, hydrocarbons containing more than 16 carbon atoms, plant oils, mineral oils, non-silicone synthetic oils, triglyceride plant oils, synthetic triglycerides, fluoro oils, liquid fatty alcohols, liquid fatty acids, liquid esters of fatty acids other than triglycerides, liquid esters of fatty alcohols other than triglycerides, liquid esters of fatty acids and fatty alcohols other than triglycerides, silicones, and mixtures thereof.

19. The agent of claim 1, further comprising at least one alkoxylated nonionic surfactant.

20. The agent of claim 19, wherein the at least one alkoxylated nonionic surfactant is selected from the group consisting of oxyethylenated fatty alcohols; polyoxyethylenated esters of saturated or unsaturated, linear or branched, C8-C30 acids and of sorbitol; polyethoxylated alkyl phenols; polypropoxylated alkyl phenols; polyethoxylated alpha-diols; polypropoxylated alpha-diols; polyethoxylated alcohols; polypropoxylated alcohols; polyethoxylated fatty amides; polyglycerolated fatty amides comprising on average 1 to 5 glycerol groups; polyethoxylated fatty amines; oxyethylenated fatty acid esters of sorbitan; and mixtures thereof.

21. The agent of claim 20, wherein the at least one alkoxylated nonionic surfactant is selected from the group consisting of laureth-23, steareth-20, ceteareth-25, polysorbate 60, laureth-2, steareth-2, and mixtures thereof.

22. The agent of claim 1, further comprising at least one fatty alcohol that is solid at 25° C.

23. The agent of claim 22, wherein the at least one fatty alcohol that is solid at 25° C. is selected from the group consisting of cetyl alcohol, cetearyl alcohol, stearyl alcohol, behenyl alcohol, and mixtures thereof.

24. The agent of claim 1, further comprising at least one auxiliary ingredient selected from the group consisting of rheology modifiers, viscosity-modifying agents, anionic surfactants, amphoteric surfactants, zwitterionic surfactants, cationic surfactants, nonionic surfactants, shine agents, fillers, colorants, pigments, chelating agents, sequestering agents, fragrances, preservatives, stabilizers, and mixtures thereof,
   wherein the nonionic surfactants are selected from the group consisting of alkylpolyglycosides, N-alkylglucamine derivatives, amine oxides, (C10-C14)alkyl amine oxides, N-acylaminopropylmorpholine oxides, and mixtures thereof.

25. An agent for shaping or altering the shape of hair, the agent comprising:
   (a) from about 0.1% to about 30% by weight of at least one alkaline material selected from at least one hydroxide-containing compound selected from the group consisting of alkali metal hydroxides, alkaline-earth metal hydroxides, transition metal hydroxides, and mixtures thereof, and wherein the at least one alkaline material is not selected from at least one carbonate compound;
(b) from about 0.1% to about 10% by weight of hexadimethrine chloride;
(c) from about 0.1% to about 10% by weight of polyquaternium-22;
(d) at least one organic solvent;
(e) water; and
(f) optionally, an activator component comprising guanidine carbonate, and optionally, a solvent;
all weights being based on the total weight of the agent for shaping or altering the shape of hair;
wherein the pH of the agent for shaping or altering the shape of hair is equal to or greater than 13;
wherein the weight ratio of (b) to (c) is from equal to or greater than 1 up to about 3; and
wherein the agent for shaping or altering the shape of hair is stable up to 8 weeks in a controlled chamber at 5° C., 25° C., 37° C., and 45° C., and for 10 days in a freeze/thaw cycle.

26. A hair treatment agent for shaping or altering the shape of hair, the hair treatment agent comprising:
(a) from about 0.1% to about 30% by weight of at least one alkaline material selected from at least one carbonate compound selected from the group consisting of lithium carbonate, sodium carbonate, potassium carbonate, guanidine carbonate, and mixtures thereof, and wherein the at least one alkaline material is not selected from at least one hydroxide-containing compound;
(b) from about 0.1% to about 10% by weight of hexadimethrine chloride;
(c) from about 0.1% to about 10% by weight of polyquaternium-22;
(d) at least one organic solvent;
(e) water; and
(f) optionally, an activator component comprising at least one hydroxide-containing compound selected from the group consisting of alkali metal hydroxides, alkaline-earth metal hydroxides, transition metal hydroxides, and mixtures thereof, and optionally, a solvent;
all weights being based on the total weight of the hair treatment agent;
wherein the pH of the agent is equal to or greater than 13;
wherein the weight ratio of (b) to (c) is from equal to or greater than 1 up to about 3; and
wherein the hair treatment agent is stable up to 8 weeks in a controlled chamber at 5° C., 25° C., 37° C., and 45° C., and for 10 days in a freeze/thaw cycle.

27. A process for shaping hair or altering the shape of hair, the process comprising the steps of:
(1) contacting hair with a shampoo having a neutral pH;
(2) rinsing the hair with water;
(3) providing a hair treatment agent for shaping or altering the shape of hair, the hair treatment agent comprising:
A. a composition containing:
(a) at least one alkaline material selected from the group consisting of:
(i) at least one hydroxide-containing compound selected from the group consisting of alkali metal hydroxides, alkaline-earth metal hydroxides, transition metal hydroxides, and mixtures thereof; and
(ii) at least one carbonate compound selected from the group consisting of lithium carbonate, sodium carbonate, potassium carbonate, guanidine carbonate, and mixtures thereof;
(b) hexadimethrine chloride;
(c) polyquaternium-22;
(d) at least one organic solvent; and
(e) water;
wherein the weight ratio of (b) to (c) is equal to or greater than 1 up to about 3;
wherein the composition is stable up to 8 weeks in a controlled chamber at 5° C., 25° C., 37° C., and 45° C., and for 10 days in a freeze/thaw cycle;
and optionally,
B. an activator component; and
wherein the agent has a pH ranging from equal to or greater than 12;
(4) applying the composition in A onto the hair, or mixing the composition in A with the activator component in B to form a mixture, then applying the mixture onto the hair;
(5) optionally brushing the hair;
(6) heating the hair at a temperature of at least 40° C. while optionally applying a smoothing action on the hair, wherein when a smoothing action is employed, the heating action and smoothing action are accomplished by use of a heating flat iron device; and
(7) rinsing the hair with water or contacting the hair with an intermediate agent having a neutral pH wherein the intermediate agent is selected from the group consisting of a shampoo and a conditioner, followed by rinsing with water.

28. The process of claim 27, wherein the process is for relaxing or straightening hair.

29. A kit for straightening or relaxing hair, the kit comprising:
I. a first unit containing a hair treatment composition containing:
(a) at least one alkaline material selected from: at least one hydroxide-containing compound selected from the group consisting of alkali metal hydroxides, alkaline-earth metal hydroxides, transition metal hydroxides, and mixtures thereof;
(b) hexadimethrine chloride;
(c) polyquaternium-22;
(d) at least one organic solvent; and
(e) water;
wherein the weight ratio of (b) to (c) is from equal to or greater than 1 up to about 3;
wherein the hair treatment composition is stable up to 8 weeks in a controlled chamber at 5° C., 25° C., 37° C., and 45° C., and for 10 days in a freeze/thaw cycle;
wherein the pH of the composition is equal to or greater than 12; and
II. a second unit containing a neutralizing composition selected from the group consisting of a shampoo and a conditioner.

30. A kit for straightening or relaxing hair, the kit comprising:
I. a first unit containing a hair treatment composition containing:
(a) at least one alkaline material selected from at least one carbonate compound selected from the group consisting of lithium carbonate, sodium carbonate, potassium carbonate, guanidine carbonate, and mixtures thereof;
(b) hexadimethrine chloride;

(c) polyquaternium-22;
(d) at least one organic solvent; and
(e) water;
   wherein the weight ratio of (b) to (c) is from equal to or greater than 1 up to about 3;
   wherein the hair treatment composition is stable up to 8 weeks in a controlled chamber at 5° C., 25° C., 37° C., and 45° C., and 10 days in a freeze/thaw cycle; and
   wherein the pH of the hair treatment composition is equal to or greater than 12; and
II. a second unit containing a neutralizing composition selected from the group consisting of a shampoo and a conditioner.

31. The kit of claim 29, wherein the alkaline material comprises calcium hydroxide.

32. The kit of claim 31, further comprising a third unit containing an activator component comprising guanidine carbonate.

33. The kit of claim 30, wherein the alkaline material comprises guanidine carbonate.

34. The kit of claim 33, further comprising a third unit containing an activator component comprising calcium hydroxide.

* * * * *